United States Patent [19]

Heckel et al.

[11] Patent Number: 5,618,814
[45] Date of Patent: Apr. 8, 1997

[54] TRISUBSTITUTED PYRIMIDO [5,4-D] PYRIMIDINES FOR MODULATING MULTI-DRUG RESISTANCE AND PHARMACEUTICAL COMPOSITIONS CONTAINING THESE COMPOUNDS

[75] Inventors: Armin Heckel, Biberach; Uwe Bamberger, Ochsenhausen; Annerose Mauz, Langenenslingen-Emerfeld, all of Germany

[73] Assignee: Dr. Karl Thomae GmbH, Biberach an der Riss, Germany

[21] Appl. No.: 284,325

[22] Filed: Aug. 2, 1994

[30] Foreign Application Priority Data

Aug. 2, 1993 [DE] Germany ............ 43 25 900.6

[51] Int. Cl.⁶ .................. A61K 31/535; C07D 487/04
[52] U.S. Cl. .................. 514/234.2; 514/228.5; 514/232.5; 544/58.2; 544/70; 544/81; 544/118; 544/256
[58] Field of Search ............ 544/118, 81, 58.2; 514/234.2

[56] References Cited

U.S. PATENT DOCUMENTS 4,329,346  5/1981  Jardillier et al. .
4,478,833  10/1984  Roch et al. ............... 544/118

FOREIGN PATENT DOCUMENTS 0023559  2/1981  European Pat. Off. .
0055444  7/1982  European Pat. Off. .
3423092  1/1986  Germany .
3833392  4/1990  Germany .

OTHER PUBLICATIONS

N. Ramu and A. Ramu, *Int'l J. Cancer*, 43. pp. 487–491 (1989) "Circumvention of Adriamycin Resistance by Dipyridamole Analogues: A Structure Activity Relationship Study".

*Primary Examiner*—Robert W. Ramsuer
*Attorney, Agent, or Firm*—Robert P. Raymond; Wendy E. Rieder; Mary-Ellen M. Devlin

[57] ABSTRACT

The invention relates to trisubstituted pyrimido [5,4-d]-pyrimidines of general formula

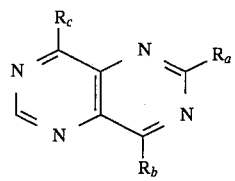

(I)

(wherein $R_a$, $R_b$ and $R_c$ are defined as in claim 1) and the salts thereof, more particularly for pharmaceutical use the physiologically acceptable salts thereof, which have, inter alia, valuable pharmacological properties, particularly in chemotherapy a sensitizing effect on resistant tumors, the use thereof and processes for preparing them.

9 Claims, No Drawings

TRISUBSTITUTED PYRIMIDO [5,4-D] PYRIMIDINES FOR MODULATING MULTI-DRUG RESISTANCE AND PHARMACEUTICAL COMPOSITIONS CONTAINING THESE COMPOUNDS

Chemotherapy for malignant diseases has achieved success as a cure only in the case of a few diseases. Any resistance present at the start of the treatment or occurring during therapy is an obstacle to improved therapeutic success. The cause and manifestation of such resistance takes many forms. However a pleiotropic resistance is frequently observed which is not restricted to specific chemical or pharmacological groups of active substances and which is usually based on the transportation of active substances out of tumour cells, leading to a reduced intracellular accumulation of active substance. A clinically significant mechanism of pleiotropic resistance, which to date has been investigated most thoroughly, is based on the expression of the transport protein gp170 (P-glycoprotein) in the membrane of tumour cells (see Ferguson and Cheng, Critical Issues Relating to Clinical Drug Resistance, Cancer Bulletin 41: 7–13 (1989)). This transport protein has a specificity for lipophilic substances and thus influences the intracellular concentration of cytostatics (which are currently of clinical importance) of the vinca-alkaloid category, of anthracyclin antibiotics, of epipodophylotoxins and of other natural substances (see van der Bliek and Borst, Multidrug Resistance, Advances in Cancer Research 52: 165–203 (1989)).

It has now been found that trisubstituted pyrimido[5,4-d]pyrimidines of the general formula

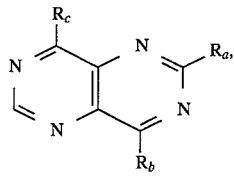

(I)

have valuable properties. When $R_a$ represents a >CO- or >($R_4$O-C-O$R_5$)- group, these compounds are valuable intermediate products for the preparation of the other compounds of general formula I which have valuable pharmacological properties, particularly in chemotherapy a sensitising effect on resistant tumours.

The present invention thus relates to the new compounds of general formula I above, the enantiomers thereof, the salts thereof, particularly the physiologically acceptable salts for pharmaceutical use, pharmaceutical compositions containing these compounds, the use thereof and processes for preparing them.

In the general formula shown above:

$R_a$ denotes a pyrrolidino, piperidino or hexamethyleneimino group in which a methylene group in the 3-position of a pyrrolidino group or in the 3- or 4-position of a piperidino or hexamethyleneimino group is replaced by a >$CR_1$-A-($R_2NR_3$)-, >CO- or >($R_4$O-C-O$R_5$)- group or by a group of formula

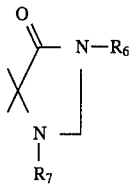

wherein

A denotes a carbon-nitrogen bond or a $C_{1-3}$-alkylene group;

$R_1$ denotes a hydrogen atom or a $C_{1-3}$-alkyl group;

$R_2$ denotes a hydrogen atom or a $C_{1-3}$-alkyl group optionally substituted by a phenyl group;

$R_3$ denotes a hydrogen atom or an optionally phenyl-substituted $C_{1-4}$-alkyl group wherein the phenyl group may be mono- or disubstituted by fluorine, chlorine or bromine atoms or by $C_{1-3}$-alkyl or $C_{1-3}$-alkoxy groups, wherein the substituents may be identical or different, or $R_3$ denotes a $C_{1-4}$-alkyl group substituted by a carboxy, alkoxycarbonyl, cyano, aminocarbonyl, alkylaminocarbonyl or dialkylaminocarbonyl group or by two phenyl groups, whilst the above-mentioned alkyl and alkoxy moieties may each contain 1 to 3 carbon atoms, or $R_3$ denotes a $C_{2-4}$-alkyl group which may be substituted in the 2-, 3- or 4-position by a hydroxy, amino, alkylamino or dialkylamino group, whilst the above-mentioned alkyl moieties may each contain 1 to 3 carbon atoms, or $R_3$ denotes an alkoxycarbonyl group having a total of 2 to 4 carbon atoms or $R_2$ and $R_3$ together with the nitrogen atom between them denote a cycloalkyleneimino group having 3 to 7 ring members, or a morpholino, thiomorpholino, 1-oxido-thiomorpholino or 1,1-dioxido-thiomorpholino group;

$R_4$ and $R_5$, which may be identical or different, represent $C_{1-3}$-alkyl groups;

or $R_4$ and $R_5$ together represent a $C_{2-3}$-n-alkylene group;

$R_6$ denotes a hydrogen atom or a $C_{1-3}$-alkyl group; and $R_7$ denotes a hydrogen atom, a $C_{1-3}$-alkyl group or a phenyl group); and $R_b$ and $R_c$, which may be identical or different, each denote a cyclic alkyleneimino group having 5 to 7 ring members to which a 1,4-butadienyl bridge may be attached via the 2-, 3- or 3-, 4-positions, and which may be mono-, di- or trisubstituted by fluorine, chlorine or bromine atoms or by alkyl, alkoxy, amino, alkylamino, dialkylamino or alkanoylamino groups, wherein the alkyl and alkoxy moieties may each contain 1 to 3 carbon atoms and the alkanoyl moiety may contain 2 or 3 carbon atoms and the substituents may be identical or different, or $R_6$ and $R_7$ may each denote a morpholino, thiomorpholino, 1-oxido-thiomorpholino, 1,1-dioxido-thiomorpholino or ($R_8NR_9$)- group, wherein $R_8$ denotes a hydrogen atom or a $C_{1-4}$-alkyl group which may be substituted by a phenyl, cyano, carboxy or alkoxycarbonyl group or in the 2-, 3- or 4-position by an amino, alkylamino, dialkylamino, alkanoylamino, benzoylamino or phenylsulphonylamino group, wherein the above-mentioned alkyl, alkoxy and alkanoyl moieties may each contain 1 to 3 carbon atoms and the phenyl nucleus in each case may be mono- or disubstituted by fluorine, chlorine or bromine atoms or by $C_{1-3}$-alkyl or $C_{1-3}$-alkoxy groups and the substituents may be identical or different, and $R_9$ denotes a hydrogen atom, or a $C_{1-4}$-alkyl group optionally substituted by a phenyl or naphthyl group, wherein the phenyl and naphthyl group may each be mono- or disubstituted by fluorine, chlorine or bromine atoms or by alkyl, alkoxy, amino, alkylamino or dialkylamino groups, (wherein the substituents may be identical or different and each alkyl and alkoxy moiety may contain 1 to 3 carbon atoms), or $R_9$ denotes a $C_{1-5}$-alkanoylamino group or an anthracenyl group, or $R_c$ may also represent an optionally phenyl-substituted $C_{1-3}$-alkoxy or $C_{1-3}$-alkylthio group.

Examples of the definitions of the groups given hereinbefore include:

for $R_a$: 3-amino-piperidino, 4-methylamino-piperidino, 4-dimethylamino-piperidino, 4-ethylamino-piperidino, 4-diethylamino-piperidino, 4-(N-methyl-ethylamino)-piperidino, 4-n-dipropylamino-piperidino, 4-benzylamino-piperidino, 4-(N-methyl-benzylamino)-piperidino, 4-(N-ethyl-benzylamino)-piperidino, 4-(N-isopropyl-benzylamino)-piperidino, 4-pyrrolidino-piperidino, 4-piperidino-piperidino, 4-(2,2-di-phenyl-ethyl)-piperidino, 4-(3,3-diphenyl-propyl)-piperidino, 4-carboxymethylamino-piperidino, 4-methoxycarbonylamino-piperidino, 4-ethoxycarbonylamino-piperidino, 4-n-propoxycarbonylamino-piperidino, 4-dimethylaminocarbonylmethylamino-piperidino, 4-(2-dimethylaminocarbonylethyl-amino)-piperidino, 4-(3-dimethylaminocarbonylpropyl-amino)-piperidino, 4-diethylaminocarbonylmethylamino-piperidino, 4-(2-diethylaminocarbonylethyl-amino)-piperidino, 4-(3-diethylaminocarbonylpropyl-amino)-piperidino, 4-di-n-propylaminocarbonylmethylamino-piperidino, 4-(2-di-n-propylaminocarbonylethyl-amino)-piperidino, 4-(3-di-n-propylaminocarbonylpropyl-amino)-piperidino-, 4-(N-carboxymethyl-methylamino)-piperidino-, 4-(N-methoxycarbonyl-methylamino)-piperidino, 4-(N-ethoxycarbonyl-methylamino)-piperidino, 4-(N-n-propoxy-carbonyl-methylamino)-piperidino, 4-(N-dimethylaminocarbonylmethyl-methylamino)-piperidino, 4-[N-(2-dimethylaminocarbonylethyl)-methylamino]-piperidino, 4-[N-(3-dimethylaminocarbonylpropyl)-methylamino]-piperidino, 4-(N-dimethylaminocarbonylpropyl)-methlamino)-piperidino, 4[N-(2-diethylaminocarbonylethyl)-methylamino]-piperidino, 4-[N-(3-n-diethylaminocarbonylpropyl)-methylamino]-piperidino, 4-(N-di-n-propylaminocarbonyl-methyl-methylamino)-piperidino, 4-[N-(2-di-n-propylaminocarbonyl-ethyl)-methlamino]-piperidino, 4-[N-(3di-n-proplaminocarbonylpropyl)-methylamino]-piperidino, 4-(N-carboxylmethyl-ethylamino)-piperidino, 4-(N-methoxycarbonylethyl)-ethylamino)-piperidino, 4-(N-ethoxycarbonyl-ethylamino)-piperidino, 4-(N-n-propoxycarbonyl-ethylamino)-piperidino, 4-(N-dimethylaminocarbonylmethyl-ethylamino)-piperidino, 4-[N-(2-dimethylaminocarbonylethyl)-ethylamino]-piperidino, 4-[N-(3-N-dimethylaminocarbonylmethyl-ethylamino)-piperidino, 4-(N-diethylaminocarbonylmethyl-ethylamino)-piperidino, 4-(N-2-diethylaminocarbonylmethyl)-ethylamino]-piperidino, 4-[N-(3-diethyl-aminocarbonylpropyl)-ethylamino]-piperidino, 4-(N-di-n-propolaminocarbonylmethyl-ethylamino)-piperidino, 4-[N-)2-di-n-propylaminocarbonylethyl)-ethylamino]-piperidino, 4-[N-(3-di-n-propylaminocarbonylpropyl)-ethylamino]-piperidino, (N-carboxymethyl-isopropylamino)-piperidino, N-(4- (N-methoxycarbonyl-n-propylmethylamino)-piperidino, 4-(N-ethoxycarbonyl-n-propylamino)-piperidino, 4-(N-n-propoxycarbonyl-isopropylamino)-piperidino, 4-(N-dimethylaminocarbonylmethyl-n-propylamino)-piperidino, 4-[N-(2-dimethylaminocarbonylethyl)-n-propylamino]-piperidino, 4-[N-(3-dimethylaminocarbonylpropyl)-n-propylamino]-piperidino, 4-(N-diethylaminocarbonylmethyl-n-propylamino)-piperidino, 4-[N-(2-diethylaminocarbonylethyl)-n-propylamino]-piperidino, 4-[N-(3-diethylaminocarbonylpropyl)-isopropylamino]-piperidino, 4-(N-di-n-propylaminocarbonylmethyl-isopropylamino)-piperidino, 4-[N-(2-di-n-propylaminocarbonylethyl)-n-propylamino]-piperidino, 4-[N-(3-di-n-propylaminocarbonylpropyl)-n-propylamino]-piperidino, 4-[N-(2-aminoethyl)-amino]-piperidino, 4-[N-(2-methylaminoethyl)-amino]-piperidino, 4-[N-(2-ethylaminoethyl)-amino]-piperidino, 4-[N-(2-isopropylamino-ethyl)-amino]-piperidino, 4-[N-(2-dimethylamino-ethyl)-amino]-piperidino, 4-[N-(2-diethylamino-ethyl)-amino]-piperidino, 4-[N-(2-di -n-propylamino-ethyl)-amino]-piperidino, 4-[N-(3-amino-propyl)-amino]-piperidino, 4-[N-(3-methylamino-propyl)-amino]-piperidino, 4-[N-(3-ethylamino-propyl)-amino]-piperidino, 4-[N-(3-isopropylamino-propyl)-amino]-piperidino, 4-[N-(3-dimethylamino-propyl)-amino]-piperidino, 4-[N-(3-diethylamino-propyl)-amino]-piperidino, 4-[N-(3-di-n-propylamino-propyl)-amino]-piperidino, 4-[N-(2-aminoethyl)-methlamino]-piperidino, 4-[N-(2-methylamino-ethyl)-methylamino]-piperidino, 4-[N-(2-ethylamino-ethyl)-methlamino]-piperidino, 4-[N-(2-isopropylamino-ethyl)-methylamino]-piperidino, 4-[N-(2-dimethylamino-ethyl)-methylamino]-piperidino, 4-[N-(2-diethylamino-ethyl)-methylamino]-piperidino, 4-[N-(2-di-n-propylamino-ethyl)-methylamino]-piperidino, 4-[N-(3-amino-propyl)-methylamino]-piperidino, 4-[N-(3-methylamino-propyl)-methylamino]-piperidino, 4-[N-(3-ethylamino-propyl)-methylamino]-piperidino, 4-[N-(3-isopropylamino-propyl)-methylamino]-piperidino, 4-[N-(3-dimethylamino-propyl)-methylamino]-piperidino, 4-[N-(3-diethlaminopropyl)-methylamino]-piperidino, 4-[N-(3-di-n-propylaminopropyl)-methylamino]-piperidino, 4-[N-(2-amino-ethyl)-ethylamino]-piperidino, 4-[N-(2-methylamino-ethyl)-ethylamino]-piperidino, 4-[N-(2-ethylamino-ethyl)-ethylamino]-piperidino, 4-[N-(2-isopropylamino-ethyl)-ethylamino]-piperidino, 4-[N-(2-dimethylamino-ethyl)-ethylamino]-piperidino, 4-[N-(2-diethylamino-ethyl)-ethylamino]-piperidino, 4-[N-(2-di-n-propylamino-ethyl)-ethylamino]-piperidino, 4-[N-(3-aminopropyl)-ethylamino]-piperidino, 4-[N-(3-methylamino-propyl)-ethylamino]-piperidino, 4-[N-(3-ethylamino-propyl)-ethylamino]-piperidino, 4-[N-(3-isopropylamino-propyl)-ethylamino]-piperidino, 4-[N-(3-dimethylamino-propyl)-ethylamino]-piperidino, 4-[N-(3-diethylamino-propyl)-ethylamino]-piperidino, 4-[N-(3-di-n-propylamino-propyl)-ethylamino]-piperidino, 4-[N-(2-amino-ethyl)-n-propylamino]-piperidino, 4-[N-(2-methylamino-ethyl)-isopropylamino]-piperidino, 4-[N-(2-ethylamino-ethyl)-isopropylamino]-piperidino, 4-[N-(2-isopropylamino-ethyl)-n-propylamino]-piperidino, 4-[N-(2 -dimethylamino-ethyl)-n-propylamino]-piperidino, 4-[N-(2 -diethylamino-ethyl)-n-propylamino]-piperidino, 4-[N-(2 -di-n-propylamino-ethyl)-n-propylamino]-piperidino, 4-[N-(3-amino-propyl)-n-propylamino]-piperidino, 4-[N-(3-methylamino-propyl)-n-propylamino]-piperidino, 4-[N-(3-ethylamino-propyl)-n-propylamino]-piperidino, 4-[N-(3-isopropylamino-propyl)-n-propylamino]-piperidino, 4-[N-(3-dimethylamino-propyl)-n-propylamino]-piperidino, 4-[N-(3-diethylamino-propyl)-n-propylamino]-piperidino, 4-[N-(3-di-n-propylamino-propyl)-n-propylamino]-piperidino, 3-amino-pyrrolidino, 3-methylamino-pyrrolidino, 3-dimethylamino-pyrrolidino, 3-diethylamino-pyrrolidino, 3-amino-hexamethyleneimino, 4-amino-hexamethyleneimino, 3-methylamino-hexamethyleneimino, 4-methylamino-hexamethyleneimino, 3-dimethylamino-hexamethyleneimino, 4-dimethylamino-hexamethyleneimino, 3-diethylamino-hexamethyleneimino and 4-diethylamino-hexamethyleneimino group, for $R_b$ and $R_c$: pyrrolidino, piperidino, hexa-methyleneimino, morpholino, thiomorpholino, 1-oxido-thiomorpholino, 1,1-dioxido-thiomorpholino, 1,2,3,4-tetrahydroisoquinolino, 1,2,3,4-tetrahydro-6,7-dimethoxyisoquinolino, methylamino, ethylamino, n-propylamino, isopropylamino, dimethylamino, diethylamino, di-n-propylamino, di-isopropylamino, benzylamino, 4-fluoro-benzylamino, 4-chloro-benzylamino, 4-bromo-benzylamino, 4-methyl-benzylamino, 4-methoxy-benzylamino, naphth-1-yl-methylamino, naphth-2-yl-methylamino, 4-fluoro-naphth-1-yl-methylamino, 4-chloro-naphth-1-yl-methylamino, 4-bromo-naphth-2-yl-methylamino, 4-methyl-naphth-2-yl-methylamino, 4-methoxy-naphth-1-yl-methylamino, 4-dimethylamino-naphth-2-yl-methylamino, N-benzyl-methylamino, N-(4-fluoro-benzyl)-methylamino, N-(4-chloro-benzyl)-methyl-amino, N-(4-bromo-benzyl)-methylamino, N-(4-methyl-benzyl)-methlamino, N-(4-methoxy-benzyl)-methylamino, N-(naphth-1-yl-methyl)-methylamino, N-(naphth-2-yl-methyl)-methylamino, N-(4-fluoro-naphth-1-yl-methyl)-methylamino, N-(4-chloro-naphth-1-yl-methyl)-methylamino, N-(4-bromo-naphth-2-yl-methyl)-methylamino, N-(4-methyl-naphth-2-yl-methyl)-methylamino, N-(4-methoxy-naphth-1-yl-methyl)-methylamino, N-(4-dimethyl-amino-naphth-2-yl-methyl)-methlamino, N-benzyl-ethylamino, N-(4-fluoro-benzyl)-ethylamino, N-(4-chloro-benzyl)-ethylamino, N-(4-bromo-benzyl)-ethylamino, N-(4-methyl-benzyl)-ethylamino, N-(4-methoxy-benzyl)-ethylamino, N-(naphth-1-yl-methyl)-ethylamino, N-(naphth-2-yl-methyl)-ethylamino, N-(4-fluoro-naphth-1-yl-methyl)-ethylamino, N-(4-chloro-naphth-1-yl-methyl)-ethylamino, N-(4-bromo-naphth-2-yl-methyl)-ethylamino, N-(4-methyl -naphth-2-yl-methyl)-ethylamino, N-(4-methoxy-naphth-1-yl-methyl)-ethylamino, N-(4-dimethylamino-naphth-2-yl-ethyl)-methylamino, N-benzyl-n-propylamino, N-(4-fluoro-benzyl)-n-propylamino, N-4-chloro-benzyl)-n-propylamino, N-(4-bromo-benzyl)-n-propylamino, N-(4-methyl-benzyl)-n-propylamino, N-(4-methoxy-benzyl)-n-propylamino, N-(naphth-1-yl-methyl)-n-propylamino, N-(naphth-2-yl-methyl)-n-propylamino, N-4-fluoro-naphth-1-yl-methyl)-n-propylamino, N-(4-chloro-naphth-1-yl-methyl)-n-propylamino, N-(4-bromo-napth-2-yl-methyl)-n-propylamino, N-(4-methyl-naphth-2-yl-methyl)-n-propylamino, N-(4-methoxy-naphth-1-yl-methyl)-n-propylamino, N-(4-dimethylamino-naphth-2-yl-ethyl)-n-propylamino, N-benzyl-isopropylamino, N-(4-fluoro-benzyl)-isopropylamino, N-(4-chloro-benzyl)-isopropylamino, N-(4-bromo-benzyl )-isopropylamino, N-(4-methyl-benzyl)-isopropylamino, N-(4-methoxy-benzyl)-isopropylamino, N-(naphth-1-yl-methyl)-isopropylamino, N-(naphth-2-yl-methyl)-isopropylamino, N-(4-fluoro-napth-1-yl-methyl)-isopropylamino, N-(4-chloro-naphth-1-yl-methyl)-isopropylamino, N-(4-bromo-naphth-2-yl-methyl)-isopropylamino, N-(4-methyl-naphth-2-yl -methyl)-isopropylamino, N-(4-methoxy-naphth-1-yl -methyl)-isopropylamino, N-(4-dimethylamino-naphth-2-yl-ethyl)-isopropylamino, N-(2-phenyl-ethyl)-amino, N-(3-phenyl-propyl)-amino, N-(2-phenyl-ethyl)-methylamino, N-(3-phenyl-propyl)-methylamino, N-(2-phenyl-ethyl)-ethylamino, N-(3-phenyl-propyl)-ethylamino, N-(2-phenyl-ethyl)-n-propylamino, N-(3-phenyl-propyl)-n-propylamino, N-(2-phenyl-ethyl)-isopropylamino, N-(3-phenyl-propyl)-isopropylamino, N-(2-cyano-ethyl)-amino, N-(3-cyano-propyl)-amino, N-(2-amino-ethyl)-amino, N-(2-methylamino-ethyl)-amino, N-(2-dimethylamino-ethyl)-amino, N-(2-diethylamino-ethyl)-amino, N-(2-di-n-proplamino-ethyl)-amino, N-(2-diisopropylamino-ethyl)-amino, N-(2-acetylamino-ethyl)-amino, N-(2-propionylamino-ethyl)-amino, N-(2-benzoylamino-ethyl)-amino, N-(2-benzenesulphonylamino-ethyl)-amino, N-(2-toluenesulphonylamino-ethyl)-amino, N-(2-cyano-ethyl)-methylamino, N-(3-cyano-propyl)-methylamino, N-(2-amino-ethyl)-methylamino, N-(2-methylamino-ethyl)-methylamino, N-(2-dimethylamino-ethyl)-methylamino, N-(2-di-n-propylamino-ethyl)-methylamino, N-(2-diisopropylamino-ethyl)-methylamino, N-(2-acetylamino-ethyl)-methylamino, N-(2-propionylamino-ethyl)-methylamino, N-(2-benzoylamino-ethyl)-methylamino, N-(2-benzenesulphonylamino-ethyl)-methylamino, N-(2-toluenesulphonylamino-ethyl)-methylamino, N-(2-cyano-ethyl)-ethylamino, N-(3-cyano-propyl)-ethylamino, N-(2-amino-ethyl)-ethylamino, N-(2-methylamino-ethyl)-ethylamino, N-(2-dimethylamino-ethyl)-ethylamino, N-(2-diethylamino-ethyl)-ethylamino, N-(2-di-n-propylamino-ethyl)-ethylamino, N-(2-diisopropylamino-ethyl)-ethylamino, N-(2-acetylamino-ethyl)-ethylamino, N-(2-propionylamino-ethyl)-ethylamino, N-(2-benzoylamino-ethyl)-ethylamino, N-(2-benzenesulphonylamino-ethyl)-ethylamino, N-(2-toluenesulphonylamino-ethyl)-ethylamino, N-(2-cyano-ethyl)-n-propylamino, N-(3-cyano-propyl)-isopropylamino, N-(2-amino-ethyl)-n-propylamino, N-(2-methylamino-ethyl)-n-propylamino, N-(2-dimethylamino-ethyl)-isopropylamino, N-(2-diethylamino-ethyl)-n-propylamino, N-(2-di-n-propylamino-ethyl)-n-propylamino, N-(2-diisopropylamino-ethyl)-n-propylamino, N-(2-acetylamino-ethyl)-n-propylamino, N-(2-propionylamino-ethyl)-n-propylamino, N-(2-benzoylamino-ethyl)-n-propylamino, N-(2-benzenesulphonylamino-ethyl)-n-propylamino, N-(2-toluenesulphonylamino-ethyl)-isopropylamino, N-(2-cyano-ethyl)-benzylamino, N-(3-cyano-propyl)-benzylamino, N-2-amino-ethyl)-benzylamino, N-(2-methylamino-ethyl)benzylamino, N-(2-dimethylamino-ethyl)-benzylamino, N-(2-diethylamino-ethyl)-benzylamino, N-(2-di-n-propylamino-ethyl)-benzylamino, N-(2-diisopropylamino-ethyl)-benzylamino, N-(2-acetylamino-ethyl)-benzylamino, N-(2-propionylamino-ethyl)-benzylamino, N-(2-benzoylamino-ethyl)-benzylamino, N-(2-benzenesulphonyl-amino-ethyl)-benzylamino, N-(2-toluenesulphonylamino-ethyl)-benzylamino, N-carboxymethyl-amino, N-methoxycarbonylmethyl-amino, N-ethoxycarbonylmethylamino, N-isopropoxycarbonylmethyl-amino, N-(2-carboxy-ethyl)-amino, N-(2-methoxycarbonyl-ethyl)-amino, N-(2-ethoxycarbonyl-ethyl)-amino, N-(2-n-propoxycarbonyl-ethyl-amino, N-(3-carboxy-propyl)-amino, N-(3-methoxycarbonyl-propyl)-amino, N-(3-ethoxycarbonyl-propyl)-amino, N-(3-isopropoxycarbonyl-propyl)-amino, N-carboxymethyl-methylamino, N-(methoxycarbonyl-methyl)-methylamino, N-(ethoxycarbonyl-ethyl)-methylamino, N-(isopropoxycarbonylmethyl)-methylamino, N-(2-carboxy-ethyl)-methylamino, N-(2-methoxycarbonyl-ethyl)-methylamino, N-(2-ethoxycarbonyl-ethyl)-methylamino, N-(2-n-propoxycarbonyl-ethyl)-methylamino, N-(3-carboxy-propyl)-methylamino, N-(3-methoxycarbonyl-propyl)-methylamino, N-(3-ethoxycarbonyl-propyl)-methylamino, N-(3-isopropoxycarbonyl-propyl)-methylamino, N-(carboxymethyl)-ethylamino, N-(methoxycarbonylmethyl)-ethylamino, N-(ethoxycarbonylmethyl)-ethylamino, N-(isopropoxycarbonylmethyl)-ethylamino, N-(2-carboxyethyl)-ethylamino, N-(2-methoxycarbonyl-ethyl)-ethylamino, N-(2-ethoxycarbonyl-ethyl)-ethylamino, N-(2-n-propoxycarbonyl-ethyl)-ethylamino, N-(3-carboxy-propyl)-ethylamino, N-(3-methoxycarbonyl-propyl)-ethylamino, N-(3-ethoxycarbonyl-propyl)-ethylamino, N-3-isopropoxycarbonyl-propyl)-ethylamino, N-(carboxymethyl)-n-propylamino, N-(methoxycarbonylmethyl)-n-propylamino, N-(ethoxycarbonylmethyl)-n-propylamino, N-(isopropoxycarbonylmethyl)-isopropylamino, N-(2-carboxy-ethyl)-n-propylamino, N-(2-methoxycarbonyl-ethyl)-isopropylamino, N-(2-ethoxycarbonyl-ethyl)-n-propylamino, N-(2-n-propoxycarbonyl-ethyl)-n-propylamino N-(3-carboxypropyl)-n-propylamino, N-(3-methoxycarbonyl-propyl)-isopropylamino, N-(3-ethoxycarbonyl-propyl)-n-propylamino, N-3-isopropoxycarbonyl-propyl)-n-propylamino, N-(carboxymethyl)-benzylamino, N-(methoxycarbonylmethyl)-benzylamino, N-(ethoxycarbonylmethyl)-benzylamino, N-(isopropoxycarbonylmethyl)-benzylamino, N-(2-carboxy-ethyl)-benzylamino, N-(2-methoxycarbonyl-ethyl)-benzylamino, N-(2-ethoxycarbonyl-ethyl)-benzylamino, N-2-n-propoxycarbonyl-ethyl)-benzylamino, N-(3-carboxy-propyl)-benzylamino, N-(3-methoxycarbonyl-propyl)-benzylamino, N-(3-ethoxycarbonyl-propyl)-benzylamino, N-3-isopropoxycarbonyl-propyl)-benzylamino, N-anthracen-9yl-amino, N-(anthracen-9-yl)-methylamino, N-(anthracen-9-yl)-ethylamino, N-(anthracen-9-yl)-n-propylamino, N-(anthracen-9-yl)-isopropylamino, N-(anthracen-9-yl)-benzylamino, 5-methoxy-1,2,3,4-tetrahydro-isoqinolin-2-yl, 6-methoxy-1,2,3,4-tetrahydro-isoquinolin-2-yl, 7-methoxy-1,2,3,4-tetrahydro-isoquinolin-2-yl, 6,7-methylenedioxy-1,2,3,4-tetrahydro-isoquinolin-2-yl, 5-acetamido-1,2,3,4-tetrahydro-isoquinolin-2-yl and 5-propionylamino-1,2,3,4-tetrahydro-isoquinolin-2-yl groups and for Rhd c: additionally methoxy, ethoxy, n-propoxy, isopropoxy, benzyloxy, 2-phenylethoxy, 3-phenylethoxy, methylthio, ethylthio, n-propylthio, isopropylthio, benzylylthio, 2-phenylethylthio and 3-phenylethylthio group.

Preferred compounds of general formula I above are those wherein $R_a$ denotes a piperidino group wherein a methylene group in the 4-position is replaced by a >$CR_1$-A-($R_2NR_3$)-, >CO- or >($R_4$O-C-$OR_5$)- group or by a group of formula

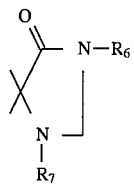

wherein

A denotes a carbon-nitrogen bond or a methylene group;

$R_1$ denotes a hydrogen atom;

$R_2$ denotes a hydrogen atom or a methyl or ethyl group;

$R_3$ denotes a hydrogen atom, or $R_3$ denotes a $C_{1-3}$-alkyl group optionally substituted by a phenyl, carboxy, methoxycarbonyl, dimethylamino or dimethylaminocarbonyl group or by two phenyl groups, or $R_3$ denotes a $C_{2-3}$-alkyl group which is substituted in the 2- or 3-position by a dimethylamino group, or $R_3$ denotes an alkoxycarbonyl group having a total of 2 to 4 carbon atoms, or $R_2$ and $R_3$ together with the nitrogen atom between them denote a pyrrolidino or piperidino group;

$R_4$ and $R_5$ together denote an ethylene group;

$R_6$ denotes a hydrogen atom; and $R_7$ denotes a phenyl group);

$R_b$ denotes a dialkylamino group wherein each alkyl moiety may contain 1 to 3 carbon atoms, or $R_b$ denotes a methylamino group substituted at the nitrogen atom by a benzyl or naphthyl group, or $R_b$ denotes a piperidino, morpholino or 1,2,3,4-tetrahydro-isoquinolyl group; and $R_c$ denotes a benzylamino group (optionally substituted at the nitrogen atom by a $C_{1-3}$-alkyl group) which may be substituted in the phenyl nucleus by a fluorine, chlorine or bromine atom or by a methyl or methoxy group and may be substituted in the alkyl moiety by a phenyl, carboxy, methoxycarbonyl, ethoxycarbonyl or cyano group or in the 2- or 3-position by an amino, acetylamino, benzoylamino or p-toluenesulphonylamino group, or $R_c$ may represent a naphthylamino group (optionally methyl-substituted at the nitrogen atom) which may be substituted in the naphthyl nucleus by a methoxy or dimethylamino group, or $R_c$ may represent a 1,2,3,4-tetrahydro-isoquinolyl group optionally substituted by a fluorine, chlorine or bromine atom or by a methyl, methoxy, methylenedioxy or acetamido group, or $R_c$ may represent a morpholino, N-methylcyclohexylmethylamino or benzyloxy group, and the salts thereof.

Particularly preferred compounds of the above general formula I are those wherein $R_a$ denotes a piperidino group in which a methylene group in the 4-position is replaced by a >$CR_1$-A-($R_2NR_3$)- group (wherein A denotes a carbon-nitrogen bond or a methylene group;

$R_1$ denotes a hydrogen atom;

$R_2$ denotes a hydrogen atom, or a methyl or ethyl group;

$R_3$ denotes a hydrogen atom, or $R_3$ denotes a $C_{2-3}$-alkyl group substituted by two phenyl groups, or $R_3$ denotes a $C_{1-3}$-alkyl group which may be substituted in the 2- or 3-position by a dimethylamino group, or $R_3$ denotes a methoxycarbonyl group, or $R_2$ and $R_3$ together with the nitrogen atom between them represent a piperidino group);

$R_b$ denotes a dimethylamino group in which a methyl group is substituted by a benzyl or naphthylmethyl group, or $R_b$ denotes a piperidino or morpholino group; and $R_c$ denotes a dimethylamino group in which a methyl group is substituted by a benzol group (optionally substituted in the phenyl nucleus by a fluorine, chlorine or bromine atom or by a methyl or methoxy group) or by a naphthylmethyl group, or $R_c$ denotes a 1,2,3,4-tetrahydro-6,7-dimethoxy-isopquinolinyl, 1,2,3,4-tetrahydro-6,7-methylenedioxy-isoquinolinyl, morpholino or N-(3-benzoylamino-propyl)-benzylamino group, wherein the groups $R_b$ and $R_c$ are different, and the salts thereof.

According to the invention, the new compounds of general formula I are obtained by the following methods:

a) reacting a compound of general formula

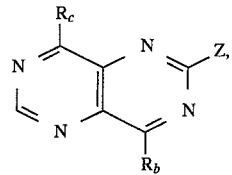 (II)

(wherein $R_b$ and $R_c$ are as hereinbefore defined and

Z denotes a leaving group such as a halogen atom, e.g. a chlorine or bromine atom, or a phenoxy or methylsulphonyl group) with a compound of general formula $$R_a\text{–H} \qquad (III)$$

wherein $R_a$ is as hereinbefore defined.

The reaction is conveniently carried out in an inert solvent such as acetone, methylethylketone, tetrahydrofuran, dioxane, chlorobenzene, dimethylformamide or dimethylsulphoxide, optionally in the presence of an inorganic base, e.g. sodium carbonate or potassium hydroxide, or a tertiary organic base, e.g. triethylamine or pyridine, whilst the latter may simultaneously serve as solvent, and optionally in the presence of a reaction accelerator such as a copper salt, a corresponding amine-hydrohalide or alkali metal halide, at temperatures between 0° and 150° C., but preferably at temperatures between 20° and 120° C. However, the reaction may also be carried out without a solvent or in an excess of the compound of general formula III.

b) In order to prepare compounds of general formula I wherein $R_a$ denotes a >CH-($R_2NR_3$)- group:

reductive amination of a compound of general formula

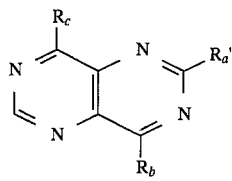

(wherein $R_b$ and $R_c$ are as hereinbefore defined and $R_a'$ denotes a pyrrolidino, piperidino or hexamethyleneimino group, wherein the methylene group in the 3-position of the pyrrolidino group or in the 3- or 4-position of the piperidino or hexamethyleneimino group is replaced by a >CO- group) with an amine of general formula $$\text{H–}R_2NR_3 \qquad (V)$$

wherein $R_2$ and $R_3$ are as hereinbefore defined.

The reductive alkylation is conveniently carried out in a solvent such as methanol, ethanol, tetrahydrofuran or dioxane, preferably in the presence of a complex metal hydride such as sodium borohydride, lithium borohydride or sodium cyanoborohydride, preferably at a pH of 6–7 and at ambient temperature or in the presence of a hydrogenation catalyst, e.g. with hydrogen in the presence of palladium/charcoal, under a hydrogen pressure of 1 to 5 bar.

If according to the invention a compound of general formula I which contains an >($R_4$OCOR$_5$)- group is obtained, this can be converted by hydrolysis into a corresponding carbonyl compound of general formula I, or if a compound of general formula I which contains an alkoxycarbonyl group is obtained, this may be converted by hydrolysis into a corresponding carboxy compound of general formula I, or if a compound of general formula I which contains a carboxy group is obtained, this may be converted by esterification or amidation into a corresponding compound of general formula I which contains an alkoxycarbonyl, aminocarbonyl, alkylaminocarbonyl or dialkylaminocarbonyl group, or if a compound of general formula I which contains a thiomorpholino group is obtained, this may be converted by oxidation into a corresponding 1-oxidothiomorpholino compound of general formula I, or if a compound of general formula I which contains a thiomorpholino or 1-oxido-thiomorpholino group is obtained, this may be converted by oxidation into a corresponding 1,1-dioxido-thiomorpholino compound of general formula I.

The optional subsequent hydrolysis is preferably carried out in an aqueous solvent, e.g. in water, isopropanol/water, tetrahydrofuran/water or dioxane/water, in the presence of an acid such as hydrochloric acid or sulphuric acid or in the presence of an alkali metal base such as sodium hydroxide or potassium hydroxide, at temperatures between 0° and 100° C., preferably at the boiling temperature of the reaction mixture.

The optional subsequent esterification and/or amidation is optionally carried out in a solvent or mixture of solvents such as methylene chloride, dimethylformamide, benzene, toluene, chlorobenzene, tetrahydrofuran, benzene/tetrahydrofuran or dioxane or, particularly advantageously, in a corresponding alcohol or amine as solvent, optionally in the presence of an acid such as hydrochloric acid or in the presence of a dehydrating agent, e.g. in the presence of isobutylchloroformate, thionylchloride, trimethylchlorosilane, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxy-benzotriazole and, in addition, optionally in the presence of 4-dimethylaminopyridine, N,N'-carbonyldiimidazole or triphenylphosphine/carbon tetrachloride, expediently at temperatures between 0° and 150° C., preferably at temperatures between 0° and 80° C.

The subsequent oxidation is preferably carried out in a solvent or mixture of solvents, e.g. in water, water/pyridine, acetone, methylene chloride, glacial acetic acid, glacial acetic acid/acetic anhydride, dilute sulphuric acid or trifluoroacetic acid, conveniently at temperatures between −80° and 100° C. depending on the oxidising agent used.

In order to prepare a corresponding 1-oxido compound of general formula I the oxidation is conveniently carried out with one equivalent of the oxidising agent used, e.g. with hydrogen peroxide in glacial acetic acid, trifluoroacetic acid or formic acid at 0° to 20° C. or in acetone at 0° to 60° C., with a peracid such as performic acid in glacial acetic acid or trifluoroacetic acid at 0° to 50° C., or with m-chloroperbenzoic acid in methylene chloride or chloroform at −20° to 60° C., with sodium metaperiodate in aqueous methanol or ethanol at −15° to 25° C., with bromine in glacial acetic acid or aqueous acetic acid, optionally in the presence of a weak base such as sodium acetate, with N-bromo-succinimide in ethanol, with tert.butyl-hypochlorite in methanol at −80° to −30° C., with iodobenzodichloride in aqueous pyridine at 0° to 50° C., with nitric acid in glacial acetic acid at 0° to 20° C., with chromic acid in glacial acetic acid or acetone at 0° to 20° C. and with sulphurylchloride in methylene chloride at −70° C., and the resulting thioether-chlorine complex is conveniently hydrolysed with aqueous ethanol.

In order to prepare a corresponding 1,1-dioxido compound of general formula I the oxidation is carried out, starting from a corresponding 1-oxido compound, conveniently with one or more equivalents of the oxidising agent used, or starting from a corresponding thio compound, preferably with two or more equivalents of the oxidising agent used, e.g. with hydrogen peroxide in glacial acetic acid/acetic anhydride, trifluoroacetic acid or in formic acid at 20° to 100° C. or in acetone at 0° to 60° C., with a peracid such as performic acid or m-chloroperbenzoic acid in glacial acetic acid, trifluoroacetic acid, methylene chloride or chloroform at temperatures of between 0° and 60° C., with nitric acid in glacial acetic acid at 0° to 20° C., with chromic acid or potassium permanganate in glacial acetic acid, water/sulphuric acid or acetone at 0° to 20° C.

In the reactions described hereinbefore, any reactive groups present such as hydroxy, amino, alkylamino or carbonyl groups may be protected during the reaction by means of conventional protecting groups which are removed by cleaving after the reaction.

For example, the protective group for a hydroxy group may be a trimethylsilyl, acetyl, benzoyl, methyl, ethyl, tert.butyl, benzyl or tetrahydropyranyl group, the protecting group for an amino, alkylamino or imino group may be an acetyl, benzoyl, ethoxycarbonyl or benzyl group and the protecting group for a carbonyl group may be a 1,3-dioxane or 1,3-dioxolane group.

The optional subsequent cleaving of the protecting group is preferably carried out hydrolytically in an aqueous solvent, e.g. in water, isopropanol/water, tetrahydrofuran/water or dioxane/water, in the presence of an acid such as hydrochloric acid or sulphuric acid or in the presence of an alkali metal base such as sodium hydroxide or potassium hydroxide at temperatures between 0° and 100° C., preferably at the boiling temperature of the reaction mixture. However, a benzyl group is preferably cleaved hydrogenolytically, e.g. using hydrogen in the presence of a catalyst such as palladium/charcoal in a solvent such as methanol, ethanol, ethyl acetate or glacial acetic acid, optionally with the addition of an acid such as hydrochloric acid at temperatures between 0° and 50° C., but preferably at ambient temperature, under a hydrogen pressure of 1 to 7 bar, preferably 3 to 5 bar.

Moreover, the compounds of general formula I obtained may be converted into the acid addition salts thereof, more particularly for pharmaceutical use into the physiologically acceptable salts thereof with organic or inorganic acids. Examples of suitable acids include hydrochloric acid, hydrobromic acid, sulphuric acid, phosphoric acid, fumaric acid, succinic acid, lactic acid, citric acid, tartaric acid and maleic acid.

In addition, the new compounds of general formula I thus obtained, if they contain a carboxy group, may if desired subsequently be converted into the salts thereof with organic or inorganic bases, more particularly for pharmaceutical use into the physiologically acceptable salts thereof. Examples of such bases include sodium hydroxide, potassium hydroxide, cyclohexylamine, ethanolamine, diethanolamine and triethanolamine.

The compounds of general formulae II to V used as starting materials are known from the literature in some cases or may be obtained by methods known from the literature.

Thus, for example, the compounds of general formulae II and IV used as starting materials are obtained by step-wise substitution of the chlorine atoms of 2,4,8-trichloro-pyrimido [5,4-d]pyrimidine (see DE-C-1 116 676).

As already mentioned hereinbefore, the new compounds of general formula I have valuable properties. Thus, the compounds of general formula I, wherein $R_a$ denotes a pyrrolidino, piperidino or hexamethyleneimino group, where a methylene group in the 3-position in a pyrrolidino group or in the 3- or 4-position in a piperidino and hexamethyleneimino group is replaced in each case by a >CO- or >($R_4OCOR_5$)- group, are valuable intermediate products for preparing the other compounds of general formula I which have valuable pharmacological properties, particularly a sensitising effect on resistant tumours during chemotherapy.

For example, this sensitisation by the following compounds:

A=2-[4-(N,N-dimethylamino)-piperidino]-8-(N-benzyl-N-methyl-amino)-4-morpholino-pyrimido [5,4-d]pyrimidine, B=2-[4-(N-methoxycarbonyl-amino-piperidino]-8-(N-benzyl-N-methyl-amino)-4-morpholino-pyrimido-[5,4-d]pyrimidine, C=2-[4-(N,N-dimethylamino)-piperidino]-8-(N-benzyl-N-methyl-amino)-4-piperidino-pyrimido [5,4-d]pyrimidine, D=8-(N-benzyl-N-methyl-amino)-2-[4-(piperidino)-piperidin-1-yl]-4-morpholino-pyrimido [5,4-d]pyrimidine, E=2-[4-(N,N-dimethylaminomethyl)-piperidino]-8-[N-(napth-1-yl-methyl)-N-methyl-amino]- 4-morpholino-pyrimido [5,4-d]pyrimidine, F=4-(N-benzyl-methyl-amino)-2-[4-(N,N-dimethylamino)-piperidino]-8-morpholino-pyrimido [5,4-d]pyrimidine, G=2-[4-(N,N-dimethylamino)-piperidino]-8-(6,7-dimethoxy-1,2,3,4-tetrahydro-isoquinolin-2-yl)-4-morpholino-pyrimido [5,4-d]pyrimidine, H=2-[4-(N,N-dimethylamino)-piperidino]-8-[N-(naphth-1-yl-methyl)-N-methyl-amino]-4-morpholino-pyrimido [5,4-d]pyrimidine, I=2-[4-(2,2-diphenylethylamino)-piperidino]-4-(N-benzyl-N-methyl-amino)-8-morpholino-pyrimido-[5,4-d] pyrimidine, J=2-[4-(N, N-dimethylamino)-piperidino]-8-[N-benzyl-N-(3-benzoylaminopropyl)-amino]-4-morpholino-pyrimido-[5,4-d]pyrimidine and K=2-[4-(N,N-dimethylamino)-piperidino]-4-[N-(naphth-1-yl-methyl)-N-methyl-amino]-8-morpholino-pyrimido-[5,4-d]pyrimidine was tested on cells resistant to adriamycin as follows:

Proliferating, adriamycin-resistant S 180 mouse sarcoma cells were cultivated for six days in the presence of various concentrations of test substances. Concentrations of the test substances with a cytotoxic or cytostatic effect were indicated by reduced cell growth or by the cells dying off. The end point of the assay is the number of living cells per culture which is determined indirectly, making use of the property of vital cells to reduce the dye MTT [=3-(4,5-dimethylthiazol-2-yl)-2,5-diphenyltetrazoliumbromide] to coloured formazane. The $IC_{50}$ denotes the concentration of a test substance which reduces the number of vital cells per culture vessel to 50% of the untreated control. The test substances were tested both in the absence of adriamycin and also in the presence of a quantity of adriamycin which does not have a proliferation-inhibiting effect under the culture conditions. Therefore, two $IC_{50}$ values are obtained for each test substance, one in the presence of adriamycin (IC50 ADR), the other in the absence of adriamycin (IC50). The difference in the logarithms (to the base ten) of the two IC50 values: $\Delta = lgIC50 - lgIC50\ ADR$ is a measure of the increase in the cytotoxicity of the test substance brought about by adriamycin.

Test procedure:

Exponentially growing adriamycin-resistant or adriamycin-sensitive S 180 cells were plated out in 96-well flatbottomed microtitre dishes at a rate of 2000 cells per well in 100 μl of growth medium (RPMI-1640 containing 10% foetal calf serum). The culture dishes were incubated in an incubator at 37° C., 5% $CO_2$ at 100% relative humidity. After 24 hours, 50 μl of growth medium containing various concentrations of test substance and 50 μl of growth medium with or without adriamycin were added to each well. Following a further 6-day cultivation period, 50 μl of tetrazolium salt solution [5 mg of 3-(4,5-dimethylthiazol-2-yl)-2, 5-diphenyl-tetrazoliumbromide per ml of phosphate-buffered saline solution, diluted 1:5 (v/v) with RPMI-1640 before use] were pipetted into each well. After 4 days' incubation the culture medium was carefully suction filtered and the formazane formed intracellularly was solubilised with 150 μl of dimethylsulphoxide per well. The dishes were briefly shaken and the optical density was measured at 570 nm with a photometer such as a Dynatech MR-600 apparatus. The formation of the coloured formazane by reduction of the tetrazolium salt is proportional to the number of living cells. The averages of three measurements were used to calculate the IC50 values (dilution stage: 1:2).

| Substance | IC50 [μg/ml] Adriamycin in ng/ml | | 1 g IC50 |
| --- | --- | --- | --- |
|  | 0 | 100 | IC50 100 ng Adriamycin |
| A | 1 | 0.3 | 0.53 |
| B | 10 | 1.0 | 1.00 |
| C | 2 | 0.3 | 0.82 |
| D | 3 | 0.3 | 1.00 |
| E | 3 | 0.1 | 1.48 |
| F | 3 | 0.3 | 1.00 |
| G | 3 | 0.1 | 1.48 |
| H | 3 | 0.1 | 1.48 |
| I | 10 | 0.3 | 1.52 |
| J | 3 | 0.1 | 1.48 |
| K | 3 | 0.1 | 1.48 |

The pyrimido[5,4-d]pyrimidines of general formula I above thus exhibit marked sensitisation to adriamycin-resistant sarcoma cells and are therefore suitable for use, optionally in conjunction with a chemotherapeutic agent, for sensitising tumours which are resistant to chemotherapy, i.e. their resistance to the particular chemotherapy is removed and in this way remission of the tumours resistant to these substances is brought about. Examples of chemotherapeutic agents include vinca alkaloids such as vinblastin, vincristin or vindesin, epipodophyllotoxins such as VP16 or anthracyllin-antibiotics such as daunorubicin, doxorubicin or bleomycin, colchicin, mitoxantron, taxol, taxotere, mithramycin or mitomycin.

The above-mentioned new pyrimido[5,4-d]pyrimidines of formula I, in conjunction with a chemotherapeutic agent, thus prevent therapy-resistant tumour cell sub-populations from surviving therapy and causing a relapse.

The pyrimido[5,4-d]pyrimidines of general formula I are well tolerated, since administration of compound G, for example, in a dose of 100 mg/kg i.v. in mice did not lead to any detectable toxic side effects.

The new pyrimido[5,4-d]pyrimidines according to the invention are preferably administered separately and, appropriately, some days (e.g. one or two days) before the administration of a chemotherapeutic agent or in conjunction with a chemotherapeutic agent administered in the usual dose; the dose of the pyrimido[5,4-d]-pyrimidine used is between 1 and 50 mg/kg of body weight per day, preferably between 3 and 20 mg/kg of body weight per day, divided up into 1 to 4 single doses. However, the drug is preferably administered by infusion.

For combined administration with a suitable chemotherapeutic agent an intravenous preparation such as an ampoule preparation is suitable; for separate administration, earlier administration or parallel administration, preparations in the form of plain or coated tablets, suspensions, syrups, capsules or suppositories are suitable.

For example, on the basis of the administration protocols known from the literature for the natural products used in the chemotherapy of neoplastic diseases (see Goodman and Gilman's, The Pharmacological Basis of Therapeutics, Macmillan Publishing Company, New York, 7th Edition, pages 1240–1247 and 1277–1289 (1985)) the first administration of a pyrimido[5,4-d]pyrimidine of formula I or a physiologically acceptable acid addition salt thereof conveniently takes place before or together with administration of the chemotherapeutic agent used or before or together with administration of a combination of several chemotherapeutic agents (see DeVita et al. in "Cancer, Principles & Practice of Oncology", 2nd Edition, J. B. Lippincott Company Philadelphia).

Further doses of a pyrimido[5,4-d]pyrimidine of formula I or a physiologically acceptable acid addition salt thereof may be given by oral route or, again, by intravenous route depending on the circumstances.

A combined preparation which is suitable for i.v. administration according to the invention thus usefully contains 1 to 25 mg/kg, preferably 1 to 20 mg/kg of body weight of a pyrimido[5,4-d]pyrimidine of formula I or a physiologically acceptable acid addition salt thereof and a suitable chemotherapeutic agent or a combination of various suitable chemotherapeutic agents.

The Examples which follow are intended to illustrate the invention:

Preparation of the starting compounds:

EXAMPLE I 2,8-Dichloro-4-morpholino-pyrimido[5,4-d]pyrimidine 9 g of 2,4,8-Trichloro-pyrimido[5,4-d]pyrimidine are suspended in 70 ml of acetone and 3.3 g of morpholine in 10 ml of acetone are added at 0° C. The reaction mixture is stirred for one hour whilst cooling with ice and then poured onto 100 ml of water. The precipitate formed is suction filtered, washed with water and dried in a desiccator. Yield: 9.5 g (81% of theory).

The following are prepared analogously:

2,8-dichloro-4-diethylamino-pyrimido[5,4-d]pyrimidine $R_f$ value: 0.45 (silica gel; methylene chloride)

2,8-dichloro-4-[N-(naphth-1-yl-methyl)-N-methyl-amino]pyrimido [5,4-d]pyrimidine 2,8-dichloro-4-(1,2,3,4-tetrahydro-isoquinolin-2-yl)-pyrimido [5,4-d]pyrimidine 2,8-dichloro-4-piperidino-pyrimido [5,4-d]-pyrimidine $R_f$ value: 0.66 (silica gel; cyclohexane/ethyl acetate=2:1)

4-benzylamino-2,8-dichloro-pyrimido[5,4-d]pyrimidine

EXAMPLE II

2-Chloro-8-(6,7-dimethoxy-1,2,3,4-tetrahydro-isoquinolin-2-yl)-4-morpholino-pyrimido [5,4-d]pyrimidine 1 g (3.2 mMol) of 2,8-dichloro-4-morpholino-pyrimido [5,4-d]pyrimidine is dissolved in 15 ml of acetone and 1.9 g (8.1 mMol) of 6,7-dimethoxy-1,2,3,4-tetrahydro-isoquinoline in a little acetone is added at ambient temperature. After 3 hours' stirring, the mixture is poured onto 20 ml of water and the precipitate is suction filtered and dried.

Yield: 1.2 g (83% of theory), $R_f$ value: 0.30 (silica gel; cyclohexane/ethyl acetate=2:1)

The following are prepared analogously:

8-(N-benzyl-N-methyl-amino)-2-chloro-4-morpholino-pyrimido[5,4-d]pyrimidine $R_f$ value: 0.60 (silica gel; cyclohexane/ethyl acetate=2:1)

2-chloro-4-morpholino-8-(1,2,3,4-tetrahydro-isoquinolin-2-yl)-pyrimido [5,4-d]pyrimidine $R_f$ value: 0.50 (silica gel; cyclohexane/ethyl acetate=2:1)

2-chloro-8-[N-(4-methoxy-benzyl)-N-methyl-amino]-4-morpholino-pyrimido [5,4-d]pyrimidine Melting point: 157°–158° C.

2-chloro-8-[N-(4-methyl-benzyl)-N-methyl-amino]-4-morpholino-pyrimido [5,4-d]pyrimidine Melting point: 156°–157° C.

2-chloro-8-[N-(4-chloro-benzyl)-N-methyl-amino]-4-morpholino-pyrimido [5,4-d]pyrimidine Melting point: 149°–151° C.

2-chloro-8-(N-cyclohexylmethyl-N-methyl-amino)-4-morpholino-pyrimido [5,4-d]pyrimidine Melting point: 98°–100° C.

2-chloro-4-morpholino-8-[N-(naphth-2-yl-methyl)-N-methyl-amino]-pyrimido [5,4-d]pyrimidine Melting point: 132°–134° C.

2-chloro-8-[N-(4-methoxy-naphth-1-yl-methyl)-N-methyl-amino]-4-morpholino-pyrimido [5,4-d]pyrimidine Melting point: 131°–135° C.

2-chloro-8-[N-(4-N,N-dimethylamino-naphth-1-yl-methyl)-N-methylamino]-4-morpholino-pyrimido [5,4-d]pyrimidine Melting point: 145°–148° C.

2-chloro-8-[N-(naphth-1-yl-methyl)-N-methylamino]-4-piperidin-1-yl-pyrimido [5,4-d]pyrimidine $R_f$ value: 0.62 (silica gel; cyclohexane/ethyl acetate=2:1)

2-chloro-8-(N-benzyl-N-ethyl-amino)-4-morpholino-pyrimido [5,4-d]pyrimidine Melting point: 108°–110° C.

2-chloro-4-morpholino-8-(3-phenylpropylamino)-pyrimido[5,4-d]pyrimidine Melting point: 100°–102° C.

2-chloro-4-morpholino-8-(2-phenylethylamino)-pyrimido [5,4-d]pyrimidine Melting point: 141°–143° C.

2-chloro-8-(cyclohexylmethylamino)-4-morpholino-pyrimido [5,4-d]pyrimidine Melting point: 125°–127° C.

8-benzyl amino-2-chloro-4-morpholino-pyrimido[5,4-d]pyrimidine Melting point: 148°–151° C.

2-chloro-8-(4-methyl-benzylamino)-4-morpholino-pyrimido[5,4-d]pyrimidine Melting point: 180°–182° C.

2-chloro-8-(4-methoxy-benzylamino)-4-morpholino-pyrimido[5,4-d]pyrimidine Melting point: 156°–158° C.

8-(N-benzyl-N-methyl-amino)-2-chloro-4-diethylamino-pyrimido[5,4-d]pyrimidine Oil, $R_f$ value: 0.52 (silica gel; methylene chloride)

2-chloro-8-[N-(naphth-1-yl-methyl)-N-methylamino]-4-morpholino-pyrimido[5,4-d]pyrimidine Oil, $R_f$ value: 0.42 (silica gel; cyclohexane/ethyl acetate=2:1)

2-chloro-4-morpholino-8-(1,2,3,4-tetrahydro-isoquinolin-2-yl)-pyrimido [5,4-d]pyrimidine Oil, $R_f$ value: 0.40 (silica gel; cyclohexane/ethyl acetate=2:1)

8-(N-benzyl-N-methyl-amino)-2-chloro-4-piperidino-pyrimido[5,4-d]pyrimidine Oil, $R_f$ value: 0.79 (silica gel; cyclohexane/ethyl acetate=2:1)

8-benzyloxy-2-chloro-4-morpholino-pyrimido-[5,4-d]pyrimidine $R_f$ value: 0.45 (silica gel; cyclohexane/ethyl acetate =2:1)

2-chloro-4,8-bis (morpholino) -pyrimido [5,4-d]pyrimidine $R_f$ value: 0.16 (silica gel; methylene chloride/methanol =39:1)

8-(N-benzyl-N-ethyloxycarbonylmethyl-amino)-2-chloro-4-piperidino-pyrimido [5,4-d]pyrimidine From N-benzylglycinethylester and 2,8-dichloro-4-morpholino-pyrimido [5,4-d]pyrimidine Melting point: 87°–91° C.

8-[N-benzyl-N-(2-cyanoethyl)-amino]-2-chloro-4-piperidino-pyrimido [5,4-d]pyrimidine From 3-benzylaminopropionitrile and 2,8-dichloro-4-morpholino-pyrimido [5,4-d]pyrimidine Melting point: 108°–112° C.

8-[N-(anthracen-9-yl)-N-methyl-amino]-2-chloro-4-morpholino-pyrimido [5,4-d]pyrimidine $R_f$ value: 0.91 (silica gel; methylene chloride/methanol =9:1)

8-(N-benzyl-N-isopropyl-amino)-2-chloro-4-morpholino-pyrimido[5,4-d]pyrimidine $R_f$ value: 0.64 (silica gel; cyclohexane/ethyl acetate =2:1)

2-chloro-8-dibenzylamino-4-morpholino-pyrimido[5,4-d]pyrimidine $R_f$ value: 0.62 (silica gel; cyclohexane/ethyl acetate =2:1)

2-chloro-4-(N-benzyl-N-methyl-amino)-8-morpholino-pyrimido[5,4-d]pyrimidine $R_f$ value: 0.52 (silica gel; cyclohexane/ethyl acetate =2:1)

2-chloro-8-[2-(3,4-dimethoxyphenyl)ethyl-methylamino]-4-morpholino-pyrimido [5,4-d]pyrimidine $R_f$ value: 0.71 (silica gel; methylene chloride/methanol= 9:1)

2-chloro-8-(isoindolin-2-yl)-4-morpholino-pyrimido[5,4-d]pyrimidine Melting point:

2-chloro-8-(5-methoxy-1,2,3,4-tetrahydroisoquinolin-2-yl)-4-morpholino-pyrimido [5,4-d]pyrimidine $R_f$ value: 0.66 (silica gel; cyclohexane/ethyl acetate=2:1)

2-chloro-8-benzylthio-4-morpholino-pyrimido-[5,4-d]pyrimidine $R_f$ value: 0.72 (silica gel; methanol/methylene chloride=50:1)

2-chloro-8-(5-acetylamino-1,2,3,4-tetrahydroisoquinolin-2-yl)-4-morpholino-pyrimido [5,4-d]pyrimidine $R_f$ value: 0.55 (silica gel; methylene chloride/methanol= 9:1)

2-chloro-8-(6,7-dihydroxy-1,2,3,4-tetrahydroisoquinolin-2-yl)-4-morpholino-pyrimido [5,4-d]pyrimidine Melting point: 194°–197° C.

2-chloro-8-(6,7-methylenedioxy-1,2,3,4-tetrahydroisoquinolin-2-yl)-4-morpholino-pyrimido-[5,4-d]pyrimidine Prepared from 2-chloro-8-(6,7-dihydroxy-1,2,3,4-tetrahydro-isoquinolin-2-yl)-4-morpholino-pyrimido [5,4-d]pyrimidine by alkylation with bromochloromethane in dimethylformamide. Melting point: 187°–189° C.

Preparation of the end products:

EXAMPLE 1

2-[4-(N,N-Dimethylamino)-piperidino]-8-(6,7-dimethoxy-1,2,3,4-tetrahydro-isoquinolin-2-yl)-4- morpholino pyrimido [5,4-d]pyrimidine 1.2g (2.7 mMol) of 2-chloro-8-(6,7-dimethoxy-1,2,3,4-tetrahydro-isoquinolin-2-yl)-4- morpholino-pyrimido[5,4-d] pyrimidine are dissolved in 20 ml of dioxane, 1.4 g (11 mMol) of 4-dimethylamino-piperidine are added and the mixture is refluxed for 4 hours. Then the solution is poured onto water and the product is extracted with ethyl acetate. The organic phase is dried over sodium sulphate and concentrated by rotary evaporation. The residue is purified by chromatography over a silica gel column with methylene chloride/methanol/ammonia =30:1:0.1. Yield: 0.5 g (36 % der Theorie), Melting point: 125° C. $C_{28}H_{38}N_8O_3$ (534.67)

|        | C     | H    | N     |
|--------|-------|------|-------|
| Calc.: | 64.59 | 7.36 | 18.86 |
| Found: | 64.31 | 7.22 | 19.03 |

The following are prepared analogously:

(1) 2-[4-(N,N-dimethylamino)-piperidino]-8-(N-benzyl-N-methylamino)-4-morpholino-pyrimido [5,4- d]pyrimidine Yield: 50% of theory, Melting point: 98° C. $C_{25}H_{34}N_8O$ (462.60)

|        | C     | H    | N     |
|--------|-------|------|-------|
| Calc.: | 64.93 | 7.41 | 24.23 |
| Found: | 64.77 | 7.52 | 24.18 |

(2) 2-[4-(N,N-dimethylamino)-piperidino]- 8-(1,2,3,4-tetrahydro-isoquolin-2-yl)-4-morpholino -pyrimido[5,4-d]pyrimidine Yield: 20% of theory Melting point: 145° C. $C_{26}H_{34}N_8O$ (474.61)

|        | C     | H    | N     |
|--------|-------|------|-------|
| Calc.: | 59.56 | 6.47 | 19.84 |
| Found: | 59.57 | 6.69 | 19.68 |

(3) 2-[4-(N,N-dimethylamino)-piperidino]-8-[N-(4-methoxy-benzyl)-N-methyl-amino]-4-morpholino-pyrimido [5,4-d]pyrimidine Yield: 33.8% of theory, Melting point: 109°–110° C. $C_{26}H_{36}N_8O$ (492.63)

|        | C     | H    | N     |
|--------|-------|------|-------|
| Calc.: | 63.39 | 7.37 | 22.75 |
| Found: | 63.14 | 7.34 | 22.44 |

(4) 2- [4-(N,N-dimethylamino)-piperidino]-8-[N-(4-methyl-benzyl)-N-methlamino]-4-morpholino-pyrimido [5,4-d]pyrimidine Yield: 33% of theory, Melting point: 234°–235° C. $C_{26}H_{36}N_8O$ (476.63)

|        | C     | H    | N     |
|--------|-------|------|-------|
| Calc.: | 64.30 | 7.68 | 23.08 |
| Found: | 64.12 | 7.65 | 22.83 |

(5) 2-[4-(N,N-dimethylamino)-piperidino]-8-[N-(4-chloro-benzyl)-N-metlamino]- 4-morpholino-pyrimido [5,4-d]pyrimidine Yield: 51.7% of theory, Melting point: 215°–220° C. $C_{25}H_{33}ClN_8O$ (497.05)

|        | C     | H    | N     |
|--------|-------|------|-------|
| Calc.: | 60.41 | 6.69 | 22.55 |
| Found: | 60.42 | 6.69 | 22.33 |

(6) 2- [4-(N,N-dimethylamino)-piperidino]-8-[N-(naphth-2-yl-methyl)-N-methlamino]-4-morpholino-pyrimido[5,4-d]pyrimidine Yield: 57.5% of theory, Melting point: 114°–117° C. $C_{29}H_{36}N_8O$ (512.66)

|        | C     | H    | N     |
|--------|-------|------|-------|
| Calc.: | 67.94 | 7.08 | 21.86 |
| Found: | 67.84 | 7.11 | 21.69 |

(7) 2-[4-(N,N-dimethylamino)-piperidino]-8-[N-(4-methoxy-napth-2-yl-methyl)-N-methyl-amino]-4-morpholino-pyrimido[5,4-d]pyrimidine Yield: 54.4% of theory, Melting point: about 130° C. $C_{30}H_{38}N_8O_2$ (542.69)

|        | C     | H    | N     |
|--------|-------|------|-------|
| Calc.: | 65.31 | 7.12 | 20.31 |
| Found: | 65.32 | 7.01 | 20.19 |

(8) 2-[4-(N,N-dimethylamino)-piperidino]-8-[N-(4-N,N-dimethylamino-napth-1-yl-methyl)-N-methyl- -amino] -4-morpholino-pyrimido [5,4-d]pyrimidine Yield: 35.2% of theory, Melting point: 170° C. $C_{31}H_{41}N_9O$ (555.73)

|        | C     | H    | N     |
|--------|-------|------|-------|
| Calc.: | 64.90 | 7.55 | 21.97 |
| Found: | 64.57 | 7.47 | 21.87 |

(9) 2-[4-(N,N-dimethylamino)-piperidino]- 8-(N-benzyl-N-ethylamino)-4-morpholino-pyrimido [5,4-d]pyrimidine Yield: 79% of theory, Oil $C_{26}H_{36}N_8O$ (476.63)

|        | C     | H    | N     |
|--------|-------|------|-------|
| Calc.: | 65.52 | 7.61 | 23.51 |
| Found: | 65.51 | 7.74 | 23.59 |

(10) 2-[4-(N,N-dimethylamino)-piperidino]-8-[N-(naphth-1-yl-methyl)-N-methylamino]-4-morpholino -pyrimido[5,4-d]pyrimidine Yield: 67% of theory, Melting point: 146°–148° C. $C_{29}H_{36}N_8O$ (512.66)

|        | C     | H    | N     |
|--------|-------|------|-------|
| Calc.: | 67.94 | 7.08 | 21.86 |
| Found: | 67.96 | 7.20 | 21.47 |

(11) 2-[4-(N,N-dimethylamino)-piperidino]-8-(3-phenyl-propyl-amino)-4-morpholino-pyrimido [5,4-d]pyrimidine Yield: 56% of theory, Melting point: 82°–84° C. $C_{26}H_{36}N_8O$ (476.63)

|        | C     | H    | N     |
|--------|-------|------|-------|
| Calc.: | 65.52 | 7.61 | 23.51 |
| Found: | 64.92 | 7.65 | 22.72 |

(12) 2-[4-(N,N-dimethylamino)-piperidino]-8-(2-phenyl-ethyl-amino)-4-morpholino-pyrimido [5,4-d]pyrimidine Yield: 68% of theory, Melting point:-115°–117° C. $C_{25}H_{34}N_8O$ (462.60)

|       | C     | H    | N     |
|-------|-------|------|-------|
| Calc.:| 64.91 | 7.41 | 24.22 |
| Found:| 64.60 | 7.36 | 24.16 |

(13) 2-[4-(N,N-dimethylamino)-piperidino]-8-(cyclohexylmethylamino)-4-morpholino-pyrimido [5,4-d]pyrimidine Yield: 58% of theory, Melting point: 110°14 112° C. $C_{24}H_{38}N_8O$ (454.62)

|       | C     | H    | N     |
|-------|-------|------|-------|
| Calc.:| 63.41 | 8.42 | 24.65 |
| Found:| 63.13 | 8.59 | 24.71 |

(14) 2-[4-(N,N-dimethylamino)-piperidino]-8-benzylamino-4-morpholino-pyrimido [5,4-d]pyrimidine Yield: 58% of theory, Melting point: 148°–150° C. $C_{28}H_{32}N_8O$ (448.58)

|       | C     | H    | N     |
|-------|-------|------|-------|
| Calc.:| 64.26 | 7.19 | 24.98 |
| Found:| 63.89 | 7.25 | 23.89 |

(15) 2-[4-(N,N-dimethylamino)-piperidino]-8-[N-(4-methylbenzyl)-amino]-4-morpholino-pyrimido [5,4-d]pyrimidine Yield: 47% of theory, Melting point: 142°–144° C. $C_{25}H_{34}N_8O$ (462.60)

|       | C     | H    | N     |
|-------|-------|------|-------|
| Calc.:| 64.91 | 7.41 | 24.22 |
| Found:| 64.86 | 7.52 | 24.32 |

(16) 2-[4-(N,N-dimethylamino)-piperidino]-8-[N-(4-methoxybenzyl)-amino]-4-morpholino-pyrimido [5,4-d]pyrimidine Yield: 55% of theory, Melting point: 124°–126° C. $C_{25}H_{34}N_8O_2$ (478.60)

|       | C     | H    | N     |
|-------|-------|------|-------|
| Calc.:| 62.74 | 7.16 | 23.41 |
| Found:| 62.30 | 7.30 | 23.32 |

(17) 8-(N-benzyl-N-methyl-amino)-2-[4-(piperidino)-piperidin-1-yl]-4-morpholino-pyrimido [5,4-d]pyrimidine From 2-chloro-8-(N-benzyl-N-methyl-amino)-4-morpholino-pyrimido[5,4-d]pyrimidine and 4-piperidino-piperidine Yield: 54% of theory, Melting point: 106° C. $C_{28}H_{38}N_8O$ (502.67)

|       | C     | H    | N     |
|-------|-------|------|-------|
| Calc.:| 66.91 | 7.62 | 22.29 |
| Found:| 67.02 | 7.85 | 22.33 |

(18) 8-(N-benzyl-N-methyl-amino)-2-[4-(N,N-dimethylaminomethyl)-piperidino]-4-morpholino-pyrimido [5,4-d]pyrimidine From 2-chloro-8-(N-benzyl-N-methyl-amino)-4-morpholino-pyrimido[5,4-d]pyrimidine and 4-(N,N-dimethylaminomethyl)-piperidine Yield: 30.6% of theory, Melting point: 145°–147° C. $C_{26}H_{36}N_8O$ (476.63)

|       | C     | H    | N     |
|-------|-------|------|-------|
| Calc.:| 65.52 | 7.61 | 23.51 |
| Found:| 65.24 | 7.70 | 23.59 |

(19) 8-(N-benzyl-N-methyl-amino)-4-morpholino-2-(1-phenyl-1,3,8-triazaspiro [4,5]decan-4-on-8-yl)-pyrimido[5,4-d]pyrimidine From 2-chloro-8-(N-benzyl-N-methyl-amino)-4-morpholino-pyrimido[5,4-d] pyrimidine and 1-phenyl-1,3,8-triazaspiro[4,5]decan-4-one Yield: 47% of theory, Melting point: 203°–205° C. $C_{31}H_{35}N_9O_2$ (565.68)

|       | C     | H    | N     |
|-------|-------|------|-------|
| Calc.:| 65.82 | 6.24 | 22.28 |
| Found:| 65.35 | 6.59 | 22.39 |

(20) 2-[4-(N,N-dimethylamino)-piperidino]-8-(N-benzyl-N-methyl-amino)-4-diethylamino-pyrimido [5,4-d]pyrimidine Melting point: 145°–148° C. Yield: 23.8% of theory, Melting point: about 160° C. $C_{25}H_{36}N_8$ (448.62)

|       | C     | H    | N     |
|-------|-------|------|-------|
| Calc.:| 66.93 | 8.09 | 24.98 |
| Found:| 66.85 | 8.05 | 25.30 |

(21) 2-[4-(N,N-dimethylamino)-piperidino]-4-[N-(naphth-1-yl-methyl)-N-methyl-amino]-8-morpholino-pyrimido[5,4-d]pyrimidine Yield: 78% of theory, Melting point: 124°–126° C. $C_{29}H_{36}N_8O$ (512.66)

|       | C     | H    | N     |
|-------|-------|------|-------|
| Calc.:| 67.94 | 7.08 | 21.86 |
| Found:| 68.00 | 7.21 | 21.76 |

(22) 2-[4-(N,N-dimethylamino)-piperidino]-4-(1,2,3,4-tetrahydro-isoquinolin-2-yl) -8-morpholino-pyrimido [5,4-d]pyrimidine Yield: 81% of theory, Melting point: 49°–53° C. $C_{26}H_{34}N_8O$ (474.61)

|       | C     | H    | N     |
|-------|-------|------|-------|
| Calc.:| 65.80 | 7.22 | 23.61 |
| Found:| 65.61 | 7.34 | 23.46 |

(23) 2-[4-(N,N-dimethylamino)-piperidino]-8-(N-benzyl-N-methylamino)-4-piperidino-pyrimido [5,4-d]pyrimidine Yield: 50% of theory, $C_{26}H_{36}N_8$ (460.63)

|       | C     | H    | N     |
|-------|-------|------|-------|
| Calc.:| 67.80 | 7.88 | 24.32 |
| Found:| 67.39 | 8.15 | 24.27 |

(24) 2-[4-(N,N-dimethylamino)-piperidino]-4,8-bis (N-benzyl-amino)-pyrimido [5,4-d]pyrimidine Yield: 71% of theory, Melting point: 143°–145° C. $C_{27}H_{32}N_8$ (468.61)

|  | C | H | N |
|---|---|---|---|
| Calc.: | 69.20 | 6.88 | 23.91 |
| Found: | 69.48 | 6.87 | 23.89 |

(25) 8-benzyloxy-2-[4-(N,N-dimethylamino)-piperidino]-4-morpholino-pyrimido [5,4-d]pyrimidine Yield: 19% of theory, Melting point: 186°–188° C. $C_{24}H_{31}N_7O_2$ (449.56)

|  | C | H | N |
|---|---|---|---|
| Calc.: | 64.12 | 6.95 | 21.81 |
| Found: | 64.23 | 6.96 | 21.69 |

(26) 2-[4-(N,N-dimethylamino)-piperidino]-4,8-bis(morpholino)-pyrimido [5,4-d]pyrimidine Yield: 26% of theory, Melting point: from 140° C. $C_{21}H_{32}N_8O_2$ (428.54)

|  | C | H | N |
|---|---|---|---|
| Calc.: | 56.48 | 7.67 | 25.09 |
| Found: | 56.62 | 7.53 | 24.89 |

(27) 2-[4-(N,N-dimethylamino)-piperidino]-8-(N-benzyl-N-ethoxycarbonylmethyl-amino)-4-morpholino-pyrimido [5,4-d]pyrimidine Yield: 97% of theory Melting point: 112°–115° C. $C_{28}H_{38}N_8O_3$ (534.67)

|  | C | H | N |
|---|---|---|---|
| Calc.: | 62.90 | 7.16 | 20.96 |
| Found: | 63.04 | 7.07 | 21.02 |

(28) 2-[4-(N,N-dimethylamino)-piperidino]-8-[N-benzyl-N-(2-cyano-ethyl)-amino]-4-morpholino-pyrimido [5,4-d]pyrimidine Yield: 89% of theory, Melting point: 45°–47° C. $C_{27}H_{35}N_9O$ (501.64)

|  | C | H | N |
|---|---|---|---|
| Calc.: | 64.65 | 7.03 | 25.13 |
| Found: | 64.63 | 7.10 | 25.38 |

(29) 2-[4-(N,N-dimethylaminomethyl)-piperidino]-8-[N-(napth-1-yl-methyl)-N-methyl-amino]-4-morpholino-pyrimido [5,4-d]pyrimidine Yield: 21% of theory, Melting point: 158° C. $C_{30}H_{38}N_8O$ (526.69)

|  | C | H | N |
|---|---|---|---|
| Calc.: | 68.42 | 7.27 | 21.27 |
| Found: | 68.55 | 7.48 | 21.05 |

(30) 2-[4-(N,N-dimethylaminomethyl)-piperidino]-8-[N-(napth-1-yl-methyl)-N-methyl-amino]-4-piperidino-pyrimido[5,4-d]pyrimidine Yield: 41% of theory, Melting point: 150°–151° C. $C_{31}H_{40}N_8$ (524.72)

|  | C | H | N |
|---|---|---|---|
| Calc.: | 70.56 | 7.50 | 21.94 |
| Found: | 71.04 | 7.44 | 21.68 |

(31) 4-(N-benzyl-N-methyl-amino)-2-[4-(N,N-dimethylamino)-piperidino]-8-morpholino-pyrimido [5,4-d]pyrimidine Yield: 47% of theory, Melting point: 122° C. $C_{25}H_{34}N_8O$ (462.60)

|  | C | H | N |
|---|---|---|---|
| Calc.: | 64.93 | 7.41 | 24.23 |
| Found: | 64.93 | 7.60 | 24.29 |

(32) 8-[N-(anthracen-9-yl)-N-methyl-amino]-2-[4-(N,N-dimethylamino)-pipidino]-4-morpholino-pyrimido [5,4-d]pyrimidine Yield: 18% of theory, Melting point: 168° C. $C_{33}H_{38}N_8O$ (562.72)

|  | C | H | N |
|---|---|---|---|
| Calc.: | 70.44 | 6.81 | 19.91 |
| Found: | 70.20 | 6.88 | 19.46 |

(33) 2-[4-(N-methoxycarbonyl-amino)-piperidino]-8-(N-benzyl-N-methyl-amino)-4-morpholino-pyrimido [5,4-d]pyrimidine Yield: 24% of theory, Melting point: 110° C. $C_{26}H_{34}N_8O_3$ (506.61)

|  | C | H | N |
|---|---|---|---|
| Calc.: | 61.64 | 6.76 | 22.12 |
| Found: | 61.47 | 6.91 | 22.17 |

(34) 2-[4-(N,N-dimethylamino)-piperidino]-8-(N-cycloheylmethyl-N-methyl-amino)-4-morpholino-pyrimido [5,4-d]pyrimidine Yield: 19% of theory, Melting point: about 210° C. $C_{25}H_{40}N_8O$ (468.65)

|  | C | H | N |
|---|---|---|---|
| Calc.: | 62.86 | 8.65 | 23.46 |
| Found: | 62.76 | 8.41 | 23.53 |

(35) 2-[4-(N,N-dimethylamino)-piperidino]-8-(N-benzyl-N-isopropyl-amino)-4-morpholino-pyrimido [5,4-d]pyrimidine Yield: 38% of theory, Melting point: 122°–125° C. $C_{27}H_{38}N_8O$ (490.66)

|  | C | H | N |
|---|---|---|---|
| Calc.: | 59.98 | 6.94 | 19.30 |
| Found: | 59.74 | 7.17 | 19.50 |

(36) 8-dibenzylamino-2-[4-(N,N-dimethylamino)-piperidino]-4--morpholino-pyrimido [5,4-d]pyrimidine Yield: 47% of theory, Melting point: 163° C. $C_{31}H_{38}N_8O$ (538.70)

|  | C | H | N |
|---|---|---|---|
| Calc.: | 69.12 | 7.11 | 20.80 |
| Found: | 69.01 | 7.06 | 20.34 |

(37) 2-(4-pyrrolidino-piperidin-1-yl)-8-(N-benzyl-N-methyl-amino)-4-morpholino-pyrimido [5,4-d]pyrimidine From 2-chloro-8-(N-benzyl-N-methyl-amino)-4-morpholino-pyrimido[5,4-d]pyrimidine and 4-pyrrolidino-piperidine Yield: 57% of theory, Melting point: 131°–134° C. $C_{27}H_{36}N_8O$ (488.64)

|  | C | H | N |
|---|---|---|---|
| Calc.: | 60.19 | 5.61 | 18.36 |
| Found: | 59.97 | 5.85 | 18.13 |

(38) 2-(8-aza-1,4-dioxaspiro[4,5]decan-8-yl)-8-(N-benzyl-N-methyl-amino)-4-morpholino-pyrimido [5,4-d]pyrimidine From 2-chloro-8-(N-benzyl-N-methyl-amino)-4-morpholino-pyrimido[5,4-d]pyrimidine and 8-aza-1,4-dioxaspiro-[4,5]decane Yield: 58% of theory, Melting point: 143° C. $C_{25}H_{31}N_7O_3$ (477.58)

|  | C | H | N |
|---|---|---|---|
| Calc.: | 62.88 | 6.54 | 20.53 |
| Found: | 62.89 | 6.62 | 20.47 |

(39) 2-[4-(N,N-dimethylamino)-piperidino]-8-[2-(3,4-dimethoxyphenyl)ethyl-methylamino]-4-morpholino-pyrimido[5,4-d]pyrimidine Yield: 16% of theory, Melting point: $C_{28}H_{40}N_8O_3$ (536.68)

|  | C | H | N |
|---|---|---|---|
| Calc.: | 62.66 | 7.51 | 20.88 |
| Found: | 62.63 | 7.33 | 20.92 |

(40) 2-[4-(N,N-dimethylamino)-piperidino]-8-(isoindolin-2-yl)-4-morpholino-pyrimido [5,4-d]pyrimidine Yield: 52% of theory, Melting point: $C_{25}H_{32}N_8O$ (460.59)

|  | C | H | N |
|---|---|---|---|
| Calc.: | 65.19 | 7.00 | 24.33 |
| Found: | 64.90 | 6.59 | 23.75 |

(41) 2-[4-(N,N-dimethylaminomethyl)-piperidino]-8-(6,7-dimethoxy-1,2,3,4-tetrahydro-isoquinolin -2-yl)-4-morpholino-pyrimido [5,4-d]pyrimidine Yield: 16% of theory, Melting point: $C_{29}H_{40}N_8O_3 \times 3H_2O$ (692.78)

|  | C | H | N |
|---|---|---|---|
| Calc.: | 53.75 | 6.98 | 16.17 |
| Found: | 53.91 | 6.85 | 15.54 |

(42) 2-[4-(N,N-dimethylaminomethyl)-piperidino]-8-(5-methoxy-1,2,3,4-tetrahydro-isoquinolin -2-yl)-4-morpholino-pyrimido [5,4-d]pyrimidine Yield: 32% of theory, Melting point: $C_{27}H_{36}N_8O_2$ (504.64)

|  | C | H | N |
|---|---|---|---|
| Calc.: | 64.26 | 7.19 | 22.20 |
| Found: | 64.24 | 7.51 | 22.71 |

(43) 2-(8-aza-1,4-dioxaspiro[4,5]decan)-8-(6,7-dimethoxy-1,2,3,4-tetahydroisoquinolin -2-yl)-4-morpholino-pyrimido [5,4-d]pyrimidine $R_f$ value: 0.65 (silica gel; methylene chloride/methanol =9:1)

(44) 2-[4-(N, N-dimethylamino)-piperidino]-8-benzylthio-4-morpholino-pyrimido [5,4-d]pyrimidine Yield: 30% of theory, Melting point: $C_{24}H_{31}N_7OS$ (465.63)

|  | C | H | N |
|---|---|---|---|
| Calc.: | 61.78 | 6.91 | 21.01 |
| Found: | 62.03 | 6.71 | 20.79 |

(45) 2-[4-(N,N-dimethylamino)-piperidino]-8-(5-acetylamino-1,2,3,4-tetrahydroisoquinolin -2-yl)-4-morpholino-pyrimido-[5,4-d]pyrimidine Yield: 73% of theory, Melting point: $C_{28}H_{37}N_9O_2$ (531.67)

|  | C | H | N |
|---|---|---|---|
| Calc.: | 63.26 | 7.01 | 23.71 |
| Found: | 63.12 | 6.95 | 23.94 |

(46) 2-[4-(N,N-dimethylamino)-piperidino]-8-(6,7-dihydroxy-1,2,3,4-tetrahydropisoquinolin -2-yl)-4-morpholino-pyrimido-[5,4-d]pyrimidine Yield: 57% of theory, Melting point: 194°–197° C. $C_{26}H_{34}N_8O_3$ (506.61)

|  | C | H | N |
|---|---|---|---|
| Found: | 61.64 | 6.76 | 22.12 |
| Found: | 60.86 | 6.93 | 21.95 |

(47) 2-[4-(N,N-dimethylamino)-piperidino]-8-(6,7-methlenedioxy-1,2,3,4-tetrahydroisoquinolin -2-yl)-4-morpholino-pyrimido [5,4-d]pyrimidine Yield: 91% of theory, Melting point: 99°–101° C. $C_{27}H_{34}N_8O_3$ (518.62)

|  | C | H | N |
|---|---|---|---|
| Found: | 62.53 | 6.61 | 21.61 |
| Found: | 62.05 | 6.63 | 21.19 |

(48) 2-[4-(N,N-dimethylamino)-pyrrolidino]-8-(6,7-dimethoxy-1,2,3,4-tetrahydroisoquinolin -2-yl)-4-morpholino-pyrimido [5,4-d]pyrimidine

EXAMPLE 2

2-[4-(N,N-diethylamino)-piperidino]-8-(N-benzyl-N-methyl-amino)-4-morpholino-pyrimido [5,4-d]pyrimidine 1.73 g of 2-(4-oxo-piperidin-1-yl)-8-(N-benzyl-N-methyl-amino)-4-morpholino-pyrimido [5,4-d]pyrimidine are dissolved in 20 ml of methanol and 20 ml of dioxane and mixed with 0.293 g of diethylamine. To this solution are added 0.31 g of sodium cyanoborohydride and 0.24 g of glacial acetic acid and the mixture is stirred for 7 hours at ambient temperature. Then the reaction mixture is stirred into 100 ml of water and made alkaline with 2N sodium hydroxide solution. This solution is extracted with ethyl acetate, the organic phase is separated off, dried and evaporated down. The product is purified over a silica gel column with ethyl acetate/methanol/ammonia=7:3:0.15. Yield: 570 mg (29% of theory) Oil $C_{27}H_{38}N_8O$ (490.66)

|        | C     | H    | N     |
|--------|-------|------|-------|
| Calc.: | 66.09 | 7.81 | 22.84 |
| Found: | 66.29 | 7.82 | 22.95 |

The following are prepared analogously:

(1) 2-(4-benzylamino-piperidino)-8-(N-benzyl-N-methyl-amino)-4-morpholino-pyrimido [5,4-d]pyrimidine Yield: 90% of theory, Melting point: 103°–106° C. $C_{30}H_{36}N_8O$ (524.67)

|        | C     | H    | N     |
|--------|-------|------|-------|
| Calc.: | 68.68 | 6.92 | 21.36 |
| Found: | 68.39 | 7.02 | 21.24 |

(2) 8-(N-benzyl-N-methyl-amino)-2-(4-ethylamino-piperidino)-4-morpholino-pyrimido [5,4-d]pyrimidine Yield: 65% of theory, Melting point: 92°–94° C. $C_{25}H_{34}N_8O$ (462.60)

|        | C     | H    | N     |
|--------|-------|------|-------|
| Calc.: | 64.91 | 7.41 | 24.22 |
| Found: | 64.95 | 7.61 | 24.56 |

(3) 2-[4-(2,2-diphenylethylamino)-piperidino]-4-(N-benzyl-N-methylamino)-8-morpholino-pyrimido [5,4-d] pyrimidine Yield: 61% of theory, Melting point: 106°–108° C. $C_{37}H_{42}N_8O$ (614.80)

|        | C     | H    | N     |
|--------|-------|------|-------|
| Calc.: | 72.29 | 6.89 | 18.23 |
| Found: | 71.92 | 6.98 | 18.00 |

(4) 2-[4-(3,3-diphenylpropylamino)-piperidino]-4-(N-benzyl-N-methlamino)-8-morpholino-pyrimido [5,4-d] pyrimidine Yield: 52% of theory, Melting point: 56°–58° C. $C_{38}H_{44}N_8O$ (628.83)

|        | C     | H    | N     |
|--------|-------|------|-------|
| Calc.: | 72.58 | 7.05 | 17.82 |
| Found: | 72.53 | 7.13 | 18.21 |

(5) 2-[4-(N',N'-dimethylcarbamoylmethyl-N-methylamino)-piperidino]-8-(N-benzyl-N-methyl-amino)-4-morpholino-pyrimido[5,4-d]pyrimidine From 2-(4-oxo-piperidin-1-yl)-8-(N-benzyl-N-methyl-amino)-4-morpholino-pyrimido [5,4-d]pyrimidine and N-methylglycine-(N',N'-dimethyl)-amide. Yield: 60% of theory Oil $C_{28}H_{39}N_9O_2$ (533.68)

|        | C     | H    | N     |
|--------|-------|------|-------|
| Calc.: | 63.02 | 7.37 | 23.62 |
| Found: | 62.94 | 7.50 | 23.72 |

(6) 2-(4-amino-piperidino)-8-(N-benzyl-N-methyl-amino)-4-morpholino-pyrimido [5,4-d]pyrimidine Yield: 24% of theory, Melting point: 204° C. (decomp.) $C_{23}H_{30}N_8O$ (434.55)

|        | C     | H    | N     |
|--------|-------|------|-------|
| Calc.  | 57.24 | 6.15 | 21.36 |
| Found: | 57.17 | 6.31 | 21.53 |

(7) 2-[4-[N-[2-(N',N'-dimethylamino)-ethyl]-N-methyl-amino]-piperidino]-8-(N-benzyl-N-methyl-amino)-4-morpholino-pyrimido [5,4-d]pyrimidine Yield: 60% of theory Oil $C_{28}H_{41}N_9O_2$ (519.70)

|        | C     | H    | N     |
|--------|-------|------|-------|
| Calc.: | 64.71 | 7.95 | 24.26 |
| Found: | 64.84 | 8.05 | 24.42 |

(8) 2-[4-(N-methylamino)-piperidino]-8-(6,7-dimethoxy-1,2,3,4-tetrahydroisoquolin-2-yl) -4-morpholino-pyrimido [5,4-d]pyrimidine Yield: 31% of theory, Melting point: $C_{27}H_{36}N_8O_3$ (520.64)

|        | C     | H    | N     |
|--------|-------|------|-------|
| Calc.: | 62.29 | 6.97 | 21.52 |
| Found: | 62.23 | 7.02 | 21.62 |

(9) 2-(4-aminopiperidino)-8-(6,7-dimethoxy-1,2,3,4-tetrahydro-isoquinolin-2-yl) -4-morpholino-pyrimido[5,4-d]pyrimidine Yield: 22% of theory, Melting point: $C_{26}H_{34}N_8O_3$ (506.61)

|        | C     | H    | N     |
|--------|-------|------|-------|
| Calc.: | 61.64 | 6.76 | 22.12 |
| Found: | 62.16 | 6.60 | 22.20 |

(10) 2-[4-(N,N-diethylamino)-piperidino]-8-(6,7-dimethoxy-1,2,3,4-tetrahydroisoquinolin-2-yl) -4-morpholino-pyrimido[5,4-d]pyrimidine Yield: 4% of theory, Melting point: $C_{30}H_{42}N_8O_3$ (562.72)

|        | C     | H    | N     |
|--------|-------|------|-------|
| Calc.: | 64.03 | 7.62 | 19.91 |
| Found: |       |      |       |

(11) 2-[4-(morpholin-4-yl)-piperidino]-8-(6,7-dimethoxy-1,2,3,4-tetrahydroisoquinolin -2-yl)-4-morpholino-pyrimido[5,4-d]pyrimidine Yield: 58% of theory, Melting point: $C_{30}H_{40}N_8O_4$ (576.70)

|  | C | H | N |
|---|---|---|---|
| Calc.: | 62.48 | 6.99 | 19.43 |
| Found: | 62.01 | 7.21 | 19.62 |

(12) 2-[4-(1-oxidothiomorpholin-4-yl)-piperidino]-8-(6,7-dimethoxy -1,2,3,4-tetrahydroisoquinolin-2-yl)-4-morpholino-pyrimido [5,4-d]pyrimidine Yield: 40% of theory, Melting point: $C_{30}H_{40}N_8O_4S$ (608.77)

|  | C | H | N |
|---|---|---|---|
| Calc.: | 59.14 | 6.62 | 18.41 |
| Found: | 59.10 | 6.62 | 18.59 |

EXAMPLE 3

8-(N-Benzyl-N-methyl-amino)-4-morpholino-2-(4-oxo-piperidin-1-yl)-pyrimido [5,4-d]pyrimidine 0.8 g of 2-(8-aza-1,4-dioxaspiro[4,5]decan-8-yl)-8-(N-benzyl-N-methyl-amino) -4-morpholino-pyrimido[5,4-d]pyrimidine are stirred in 40 ml of 1N HCl for 20 minutes at ambient temperature and then stirred for 10 minutes over a steam bath. After cooling, the mixture is made slightly basic with sodium hydroxide solution, extracted with ethyl acetate and the organic phase, having been washed with water and dried over sodium sulphate, is evaporated down in vacuo. The residue obtained is triturated with ether. Yield: 0.6 g (82% of theory), $C_{23}H_{27}N_7O_2$ (433.53)

|  | C | H | N |
|---|---|---|---|
| Calc.: | 64.42 | 6.28 | 22.62 |
| Found: | 64.35 | 6.10 | 22.41 |

The following is prepared analogously:
8-(6,7-dimethoxy-1,2,3,4-tetrahydroisoquinolin-2-yl)-2-(4-oxo-piperidin-1-yl) -4-morpholino-pyrimido[5,4-d]-pyrimidine $R_f$ value: 0.09 (silica gel; ethyl acetate/cyclohexane =2:1)

EXAMPLE 4

2- [4-(Carboxymethylamino)-piperidino]-8-(N-benzyl-N-methyl-amino)-4-morpholino-pyrimido [5,4-d]pyrimidine 0.5 g of 2-[4-(methyloxycarbonylmethylamino)-piperidino]-8-(N-benzyl-N-methyl-amino)-4-morpholino-pyrimido[5,4-d]pyrimidine are stirred in 10 ml of methanol and 1 ml of 1N NaOH over a steam bath for about 15 minutes. The mixture is then evaporated down in vacuo, triturated with water and the product obtained is suction filtered and dried. Yield: 0.3 g (62% of theory), Melting point: 166°–169° C. $C_{25}H_{32}N_8O_3$ (492.59)

|  | C | H | N |
|---|---|---|---|
| Calc.: | 60.96 | 6.55 | 22.75 |
| Found: | 60.78 | 6.07 | 22.77 |

The following is prepared analogously:
(1) 2-[4-(N,N-dimethylamino)-piperidino]-8-(N-benzyl-N-carboxymethyl-amino)-4-morpholino-pyrimido [5,4-d]pyrimidine Yield: 79% of theory, Melting point: 151°–155° C. $C_{26}H_{34}N_8O_3$ (506.61)

|  | C | H | N |
|---|---|---|---|
| Calc.: | 61.64 | 6.76 | 22.12 |
| Found: | 61.44 | 7.10 | 22.37 |

EXAMPLE 5

2-[4-(N,N-Dimethylamino)-piperidino]-8-[N-benzyl-N-(3-benzoylaminopropyl)-amino]-4-morpholino-pyrimido[5,4-d]-pyrimidine 0.75 g of 2-[4-(N,N-dimethylamino)-piperidino]-8-[N-benzyl-N-(3-aminopropyl)-amino]-4-morpholino-pyrimido [5,4-d]pyrimidine are dissolved in 8 ml of methylene chloride and mixed with 0.24 g of benzoyl chloride and 0.3 g of triethylamine in 2 ml of methylene chloride. The reaction mixture is stirred for 12 hours at ambient temperature and then extracted three times with water. The organic phase is dried over sodium sulphate and concentrated by rotary evaporation. The residue is chromatographed over a silica gel column using methylene chloride/methanol=7:3. Yield: 0.7 g (77% of theory) Oil $C_{34}H_{43}N_9O_2$ (609.78)

|  | C | H | N |
|---|---|---|---|
| Calc.: | 66.97 | 7.11 | 20.67 |
| Found: | 66.85 | 6.98 | 20.71 |

The following compounds are obtained analogously:
(1) 8-[N-benzyl-N-(3-acetylaminopropyl)-amino]-2-[4-(N,N-dimethylamino)-pieridino]-4-morpholino-pyrimido[5,4-d]pyrimidine Yield: 69% of theory, Melting point: 165°–167° C. $C_{29}H_{41}N_9O_2$ (547.71)

|  | C | H | N |
|---|---|---|---|
| Calc.: | 63.60 | 7.54 | 23.02 |
| Found: | 63.33 | 7.68 | 23.20 |

(2) 2-[4-(N,N-dimethylamino)-piperidino]-8-[N-benzyl-N-(3-toluensulphonamidopropyl)-amino]-4-morpholino-pyrimido[5,4-d]pyrimidine Yield: 77% of theory, Melting point: 86°–89° C. $C_{34}H_{45}N_9O_3S$ (659.86)

|  | C | H | N | S |
|---|---|---|---|---|
| Calc.: | 61.89 | 6.87 | 19.10 | 4.87 |
| Found: | 61.79 | 6.91 | 18.92 | 5.28 |

EXAMPLE 6

8-[N-Benzyl-N-(3-aminopropyl)-amino]-2-[4-(N,N-dimethylamino)-piperidino]-4-morpholino-pyrimido[5,4-d]-pyrimidine 4 g of 8-[N-benzyl-N-(2-cyano-ethyl)-amino]-2-[4-(N,N-dimethylamino)-piperidino]-4-piperidinopyrimido[5,4-d] pyrimidine are treated with hydrogen in 200 ml of ethanolic ammonia and in the presence of 0.8 g of Raney nickel. After the calculated amount of hydrogen has been taken up the catalyst is filtered off, the filtrate is evaporated down in vacuo and the residue obtained is purified over a silica gel column with methylene chloride/methanol/ammonia= 7:3:0.15. Yield: 2 g (50% of theory), Melting point: 102°–105° C. $C_{27}H_{39}N_9O$ (505.67)

|  | C | H | N |
|---|---|---|---|
| Calc.: | 64.13 | 7.77 | 24.93 |
| Found: | 64.39 | 8.00 | 25.04 |

EXAMPLE I

Coated tablets containing 75 mg of 2-[4-(N,N-dimethylamino)-piperidino]-8-(6,7-dimethoxy-1,2,3,4-tetrahydro-isoquinolin-2-yl)-4-morpholino-pyrimido-[5,4-d]pyrimidine

| 1 tablet core contains: | |
|---|---|
| Active substance | 75.0 mg |
| Calcium phosphate | 93.0 mg |
| Corn starch | 35.5 mg |
| Polyvinylpyrrolidone | 10.0 mg |
| Hydroxypropylmethylcellulose | 15.0 mg |
| Magnesium stearate | 1.5 mg |
|  | 230.0 mg |

Preparation:

The active substance is mixed with calcium phosphate, corn starch, polyvinylpyrrolidone, hydroxypropylmethylcellulose and half the specified amount of magnesium stearate. Using a tablet making machine, compressed about 13 mm in diameter tablets are produced which are then rubbed through a 1.5 mm mesh screen on a suitable machine and mixed with the remaining magnesium stearate. These granules are compressed in a tablet making machine to form tablets of the desired shape. Weight of core: 230 mg Punch: 9 mm, convex The tablet cores thus produced are coated with a film consisting essentially of hydroxypropylmethylcellulose. The finished film coated tablets are glazed with beeswax. Weight of film-coated tablet: 245 mg

EXAMPLE II

Tablets containing 100 mg of 2-[4-(N,N-dimethylamino)-piperidino]-8-(6,7-dimethoxy-1,2,3,4-tetrahydro-isoquinolin-2-yl)-4-morpholino-pyrimido [5,4-d]pyrimidine

| Composition: 1 tablet contains: | |
|---|---|
| Active substance | 100.0 mg |
| Lactose | 80.0 mg |
| Corn starch | 34.0 mg |
| Polyvinylpyrrolidone | 4.0 mg |
| Magnesium stearate | 2.0 mg |
|  | 220.0 mg |

Preparation process:

The active substance, lactose and starch are mixed together and uniformly moistened with an aqueous solution of the polyvinylpyrrolidone. After the moist mass has been screened (2.0 mm mesh size) and dried in a rack dryer at 50° C. it is screened again (1.5 mm mesh size) and the lubricant is added. The mixture produced is formed into tablets. Weight of tablet: 220 mg Diameter: 10 mm, biplanar, facetted on both sides and notched on one side.

EXAMPLE III

Tablets containing 150 mg of 2-[4-(N,N-dimethylamino)-piperidino]-8-(6,7-dimethoxy-1,2,3,4-tetrahydro-isoquinolin-2-yl)-4-morpholino-pyrimido [5,4-d]-pyrimidine

| Composition: 1 tablet contains: | |
|---|---|
| Active substance | 150.0 mg |
| Powdered lactose | 89.0 mg |
| Corn starch | 40.0 mg |
| Colloidal silica | 10.0 mg |
| Polyvinylpyrrolidone | 10.0 mg |
| Magnesium stearate | 1.0 mg |
|  | 300.0 mg |

Preparation:

The active substance mixed with lactose, corn starch and silica is moistened with a 20% aqueous polyvinylpyrrolidone solution and passed through a 1.5 mm mesh screen.

The granules dried at 45° C. are rubbed through the same screen again and mixed with the specified amount of magnesium stearate. Tablets are compressed from the mixture. Weight of tablet: 300 mg Punch: 10 mm, flat

EXAMPLE IV

Hard gelatin capsules containing 150 mg of 2-[4-(N,N-dimethylamino)-piperidino]-8-(6,7-dimethoxy-1,2,3,4-tetrahydro-isoquinolin-2-yl)-4-morpholino-pyrimido [5,4-d] pyrimidine

| 1 capsule contains: | | |
|---|---|---|
| Active substance |  | 150.0 mg |
| Dried corn starch | about | 180.0 mg |
| Powdered lactose | about | 87.0 mg |
| Magnesium stearate |  | 3.0 mg |
|  | about | 320.0 mg |

Preparation:

The active substance is mixed with the excipients, passed through a 0.75 mm mesh screen and homogeneously mixed in a suitable apparatus.

The final mixture is packed into size 1 hard gelatin capsules. Capsule contents: about 320 mg Capsule shell: size 1 hard gelatin capsule.

EXAMPLE V

Suppositories containing 150 mg of 2-[4-(N,N-dimethylamino)-piperidino]-8-(6,7-dimethoxy-1,2,3,4-tetrahydro-isoquinolin-2-yl)-4-morpholino-pyrimido-(5,4-d]pyrimidine

| 1 suppository contains: | |
|---|---|
| Active substance | 150.0 mg |
| Polyethyleneglycol 1500 | 550.0 mg |
| Polyethyleneglycol 6000 | 460.0 mg |
| Polyoxyethylene sorbitan monostearate | 840.0 mg |
|  | 2000.0 mg |

Preparation:

After the suppository mass has been melted the active substance is homogeneously distributed therein and the melt is poured into chilled moulds.

EXAMPLE VI

Suspension containing 50 mg of 2-[4-(N,N-dimethylamino)-piperidino]-8-(6,7-dimethoxy-1,2,3,4-tetrahydro-isoquinolin-2-yl)-4-morpholino-pyrimido[5,4-d]-pyrimidine

| 100 ml of suspension contain: | |
|---|---|
| Active substance | 1.0 g |
| Sodium salt of carboxymethylcellulose | 0.2 g |
| Methyl p-hydroxybenzoate | 0.05 g |
| Propyl p-hydroxybenzoate | 0.01 g |
| Sucrose | 10.0 g |
| Glycerol | 5.0 g |
| 70% Sorbitol solution | 50.0 g |
| Flavouring | 0.3 g |
| Distilled water ad | 100 ml |

Preparation:

Distilled water is heated to 70° C. The methyl and propyl p-hydroxybenzoates together with the glycerol and sodium salt of carboxymethylcellulose are disolved therein with stirring. The solution is cooled to ambient temperature and the active substance is added and homogeneously dispersed therein with stirring. After the addition and dissolution of the sugar, sorbitol solution and flavouring, the suspension is evacuated with stirring. 5 ml of suspension contain 50 mg of active substance.

EXAMPLE VII

Ampoules containing 10 mg of 2-[4-(N,N-dimethylamino)-piperidino]-8-(6,7-dimethoxy-1,2,3,4-tetrahydro-isoquinolin-2-yl)-4-morpholino-pyrimido [5,4-d]pyrimidine

| Composition: | |
|---|---|
| Active substance | 10.0 mg |
| 0.01 N hydrochloric acid q.s. | |
| Twice distilled water ad | 2.0 ml |

Preparation process:

The active substance is dissolved in the required amount of 0.01 N HCl, made isotonic with common salt, filtered sterile and transferred into 2 ml ampoules. Sterilisation is carried out by heating to 121° C. for 20 minutes.

EXAMPLE VIII

Ampoules containing 50 mg of 2-[4-(N,N-dimethylamino)-piperidino]-8-(6,7-dimethoxy-1,2,3,4-tetrahydro-isoquinolin-2-yl)-4-morpholino-pyrimido [5,4-d]pyrimidine

| Composition: | |
|---|---|
| Active substance | 50.0 mg |
| 0.01 N hydrochloric acid q.s. | |
| Twice distilled water ad | 10.0 ml |

Preparation process:

The active substance is dissolved in the required amount of 0.01 N HCl, made isotonic with common salt, filtered sterile and transferred into 10 ml ampoules. Sterilisation is carried out by heating to 121° C. for 20 minutes.

EXAMPLE IX

Dry ampoules containing 10 mg of doxorubicin and 10 mg of 2-[4-(N,N-dimethylamino)-piperidino]-8-(6,7-dimethoxy-1,2,3,4-tetrahydro-isoquinolin -2-yl)-4-morpholino-pyrimido [5,4-d]pyrimidine Composition of the dry ampoule:

| Doxorubicin | 10.0 mg |
|---|---|
| Active substance | 10.0 mg |

Preparation process:

The two active substances are dissolved in the required amount of 0.01 N HCl, filtered sterile and lyophilysed.

The solvent ampoule contains 5 ml of saline solution.

Before use the lyophilysate is dissolved in the sterile physiological saline solution.

EXAMPLE X

Dry ampoules containing 50 mg of doxorubicin and 50 mg of 2-[4-(N,N-dimethylamino)-piperidino]-8-(6,7-dimethoxy-1,2,3,4-tetrahydro-isoquinolin-2-yl) -4-morpholino-pyrimido[5,4-d]pyrimidine Composition of the dry ampoule:

| Doxorubicin | 50.0 mg |
|---|---|
| Active substance | 50.0 mg |

Preparation process:

The two active substances are dissolved in the required amount of 0.01 N HCl, filtered sterile and lyophilysed.

The solvent ampoule contains 25 ml of saline solution.

Before use the lyophilysate is dissolved in the sterile physiological saline solution.

Clearly, all other compounds of general formula I may be used as active substances in the galenic preparations described above.

What is claimed is:

1. A trisubstituted pyrimido[5,4-d]pyrimidine of formula (I)

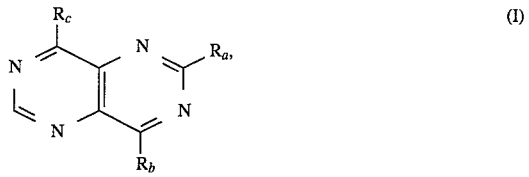

wherein $R_a$ denotes a piperidino group in which a methylene group in the 3- or 4-position is replaced by $>CR_1$-A-$(R_2NR_3)$ wherein A denotes a carbon-nitrogen bond or a $C_{1-3}$-alkylene group;

$R_1$ denotes a hydrogen atom or a $C_{1-3}$-alkyl group;

$R_2$ denotes a hydrogen atom or a $C_{1-3}$-alkyl group optionally substituted by a phenyl group;

$R_3$ denotes a hydrogen atom or $C_{1-4}$-alkyl group optionally substituted by a phenyl group;

$R_b$ denotes a morpholino group and $R_c$ denotes an -$NR_8R_9$ group wherein $R_8$ denotes a hydrogen atom or a $C_{1-4}$-alkyl group which may be substituted by a phenyl group, and $R_9$ denotes a hydrogen atom, or a $C_{1-4}$ alkyl group optionally substituted by a phenyl or naphthyl group, wherein the phenyl or naphthyl group may each be mono- or disubstituted by fluorine, chlorine or bromine atoms or by $C_{1-3}$ alkyl or $C_{1-3}$ alkoxy, or $R_c$ denotes a 1,2,3,4-tetrahydro-isoquinolinyl group which may be mono-or di-substituted by $C_{1-3}$ alkoxy, or a physiologically acceptable salt thereof.

2. The trisubstituted pyrimido[5,4-d]pyrimidine of formula (I) according to claim 1, wherein $R_1$ denotes a hydrogen atom;

$R_2$ denotes a hydrogen atom or a methyl group; and $R_c$ denotes an -$NR_8R_9$ group wherein $R_8$ denotes a hydrogen atom or a $C_{1-4}$-alkyl group which may be substituted by a phenyl group, and $R_9$ denotes a $C_{1-4}$-alkyl group optionally substituted by phenyl, 4-methyl-phenyl, 4-chloro-phenyl or naphthyl, or $R_c$ denotes a 1,2,3,4-tetrahydro-isoquinolinyl or 1,2,3,4-tetrahydro-6,7-dimethoxy-isoquinolinyl group;

or a physiologically acceptable salt thereof.

3. The trisubstituted pyrimido[5,4-d]pyrimidine of formula (I) according to claim 1 selected from the group consisting of:

(a) 2-[4-(N,N-Dimethylamino)-piperidino]-8-(N-benzyl-N-methylamino)-4-morpholino-pyrimido [5,4-d]pyrimidine;

(b) 2-[4-(N,N-Dimethylaminomethyl)-piperidino]-8-[N-(naphth-1-yl-methyl)-N-methyl-amino]-4-morpholino-pyrimido[5,4-d]pyrimidine;

(c) 2-[4-(N,N-Dimethylamino)-piperidino]-8-(1,2,3,4-tetrahydro-isoquinolin-2-yl) -4-morpholino-pyrimido[5,4-d]pyrimidine;

(d) 2-[4-(N,N-Dimethylamino)-piperidino]-8-(6,7-dimethoxy-1,2,3,4-tetrahydro-isoquinolin-2-yl) -4-morpholino-pyrimido[5,4-d]pyrimidino;

(e) 2-(4-benzylamino-piperidino)-8-(N-benzyl-N-methylamino)-4-morpholino-pyrimido [5,4-d]pyrimidine;

(f) 2-[4-(N,N-Dimethylamino)-piperidino]-8-[N-(4-methoxy-benzyl)-N-methylamino]-4-morpholino-pyrimido [5,4-d]pyrimidine;

(g) 2-[4-(N,N-Dimethylamino)-piperidino]-8-[N-(4-methyl-benzyl)-N-methyl-amino]-4-morpholino-pyrimido[5,4-d]pyrimidine;

(h) 2-[4-(N,N-Dimethylamino)-piperidino]-8-[N-(4-chloro-benzyl)-N-methyl-amino]-4-morpholino pyrimido[5,4-d]pyrimidine; and the physiologically acceptable salts thereof.

4. The trisubstituted pyrimido[5,4-d]pyrimidine 2-[4-(N,N-Dimethylaminomethyl)-piperidino]-8-[N-(naphth-1-yl-methyl)-N-methyl-amino]-4-morpholino-pyrimido [5,4-d] pyrimidine or a physiologically acceptable salt thereof.

5. The trisubstituted pyrimido[5,4-d]pyrimidine 2-[4-(N,N-Dimethylamino)-piperidino]-8-(1,2,3,4-tetrahydro-isoquinolin-2-yl)-4-morpholino-pyrimido [5,4-d]pyrimidine or a physiologically acceptable salt thereof.

6. The trisubstituted pyrimido[5,4d]pyrimidine 2-[4-(N,N-Dimethylamino)-piperidino]-8-[N-(4-methyl-benzyl)-N-methyl-amino]-4-morpholino-pyrimido [5,4-d]pyrimidine or a physiologically acceptable salts thereof.

7. The trisubstituted pyrimido[5,4-d]pyrimidine 2-[4-(N,N-Dimethylamino)-piperidino]-8-[N-(4-chloro-benzyl)-N-methyl-amino]-4-morpholino-pyrimido [5,4-d]pyrimidine or a physiologically acceptable salt thereof.

8. A pharmaceutical composition comprising a trisubstituted pyrimido[5,4d]pyrimidine according to any one of claims 1, 2, 3, 4, 5, 6 or 7 and one or more inert carriers.

9. A method for enhancing the effect ot chemotherapy in a warm-blooded animal which comprises the step of administering to said animal a therapeutically effective amount of the pharmaceutical cramposition according to claim 8.

* * * * *